Figure 1:
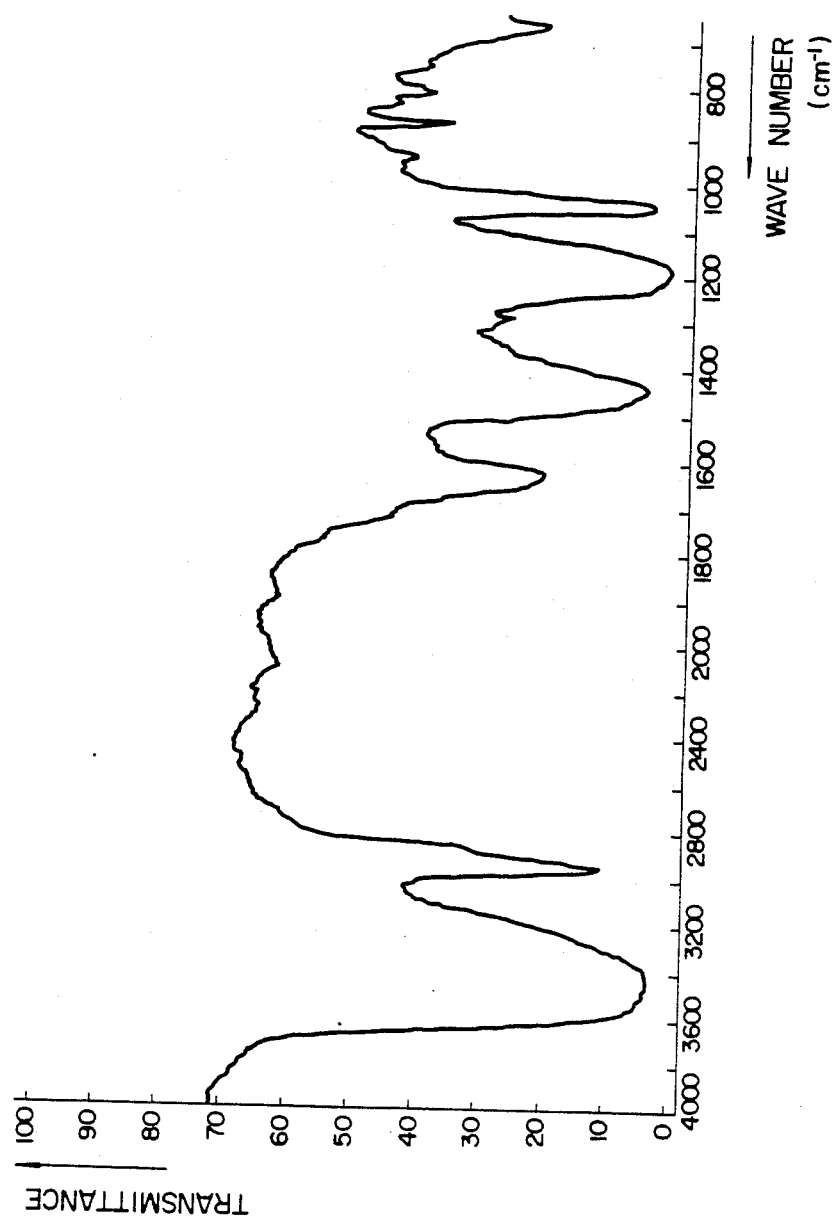

United States Patent [19]

Shinohara et al.

[11] Patent Number: 4,511,683
[45] Date of Patent: Apr. 16, 1985

[54] SULFONIC ACID COMPOUND HAVING CYCLOPENTADIENE SKELETON AND COMPOSITION COMPRISING SAME AND CEMENT

[75] Inventors: Hironobu Shinohara; Noboru Yamahara; Yoshinori Yoshida, all of Yokkaichi, Japan

[73] Assignee: Japan Synthetic Rubber Co., Ltd., Tokyo, Japan

[21] Appl. No.: 471,671

[22] Filed: Mar. 3, 1983

[30] Foreign Application Priority Data

| Mar. 8, 1982 | [JP] | Japan | 57-35147 |
| Mar. 8, 1982 | [JP] | Japan | 57-35148 |
| Mar. 8, 1982 | [JP] | Japan | 57-35149 |
| Mar. 9, 1982 | [JP] | Japan | 57-35731 |
| Mar. 9, 1982 | [JP] | Japan | 57-35732 |
| Mar. 12, 1982 | [JP] | Japan | 57-38099 |
| Oct. 4, 1982 | [JP] | Japan | 57-174400 |
| Oct. 6, 1982 | [JP] | Japan | 57-175666 |

[51] Int. Cl.[3] .............................................. C08K 3/00
[52] U.S. Cl. ................................... 524/3; 524/157; 525/154; 525/332.1; 526/287
[58] Field of Search .................. 524/3, 157; 525/332.1, 525/154; 526/287

[56] References Cited

U.S. PATENT DOCUMENTS 3,642,728  2/1972  Canter ............................. 525/331.8
4,064,040  12/1977  Singhal et al. ...................... 210/643

Primary Examiner—Joseph L. Schofer
Assistant Examiner—N. Sarofim
Attorney, Agent, or Firm—Oblon, Fisher, Spivak, McClelland & Maier

[57] ABSTRACT

Compounds having a cyclopentadiene skeleton and at least one sulfonic acid group are novel, and produced by subjecting cyclopentadiene, dicyclopentadiene and/or hydroxydicyclopentadiene to sulfonation, and subjecting the same, before or after the sulfonation, to reaction with alkylbenzene, polymerization and/or condensation through an aldehyde. The aforesaid compounds are useful as dispersants for cement.

By incorporating a polymer emulsion into a slurry composition comprising a powder and a dispersant having at least one sulfonic acid group the proportion of said polymer emulsion being 0.05 to 50 parts by weight per 100 parts by weight of said dispersant, the dispersing effect of said dispersant is improved, the fluidizing effect of the dispersant is further enhanced, the slump loss is made very small, and the workability becomes good.

9 Claims, 6 Drawing Figures

SULFONIC ACID COMPOUND HAVING CYCLOPENTADIENE SKELETON AND COMPOSITION COMPRISING SAME AND CEMENT

This invention relates to a compound having a cyclopentadiene skeleton and at least one sulfonic acid group.

In general, sulfonic acid and its derivatives, which are organic compounds, are strong acids comparable with sulfuric acid, and are industrially used in a wide field taking advantage of their properties. And their salts are water-soluble and hence very important as surfactants for organic or inorganic materials.

However, many of sulfonation products which have heretofore been synthesized are those of aromatic or aliphatic compounds, and substantially no sulfonation products of alicyclic compounds are known.

The present inventors have conducted extensive research on sulfonation products obtained by using alicyclic compounds and their derivatives as starting materials to find that compounds having a cyclopentadiene skeleton and at least one sulfonic acid group can be produced, and that the obtained compounds or their salts are water-soluble, and hence have an excellent surface-active effect on organic and inorganic materials and have a particularly excellent effect on the dispersing of cement in water.

According to this invention, there is provided a compound having a cyclopentadiene skeleton and at least one sulfonic acid group and is also provided a composition comprising the same and cement.

The compound having a cyclopentadiene skeleton and at least one sulfonic acid group include the following:

(1) Sulfonation products of polymers of cyclopentadiene derivatives represented by the formula (A) or (B)

(A)

wherein $R_1$ is a hydrogen atom or an alkyl group having 1 to 3 carbon atoms,

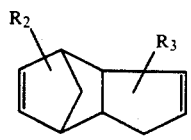
(B)

wherein $R_2$ and $R_3$, which may be the same or different, represent hydrogen atoms or alkyl groups having 1 to 3 carbon atoms.

(2) Sulfonation products obtained by sulfonating a reaction mixture prepared by reacting a cyclopentadiene derivative represented by the formula (A) or (B) with a compound represented by the formula (C):

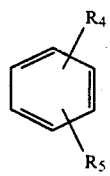
(C)

wherein $R_4$ and $R_5$, which may be the same or different, represent hydrogen atoms or alkyl groups having 1 to 6 carbon atoms.

(3) Condensates obtained by condensing in the presence of an aldehyde a sulfonation product prepared by sulfonating a reaction mixture obtained by reacting a cyclopentadiene derivative represented by the formula (A) or (B) with a compound represented by the formula (C).

(4) Condensates obtained by condencing in the presence of an aldehyde a sulfonated cyclopentadiene derivative represented by the formula (D):

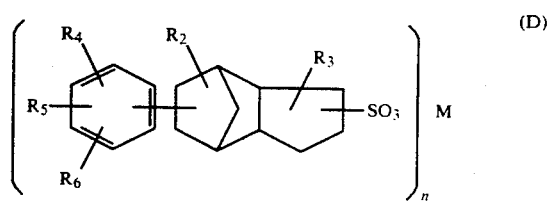
(D)

wherein $R_2$, $R_3$, $R_4$ and $R_5$ are the same as defined above; $R_6$ is a hydrogen atom or an alkyl group having 1 to 6 carbon atoms, and $R_4$, $R_5$ and $R_6$ may be the same as or different from one another; M is hydrogen, an alkali metal, an alkaline earth metal, ammonium or an amine; and n is 1 or 2 and when M is an alkaline earth metal atom n is 2.

(5) Disulfonated cyclopentadiene derivatives represented by the formula (E):

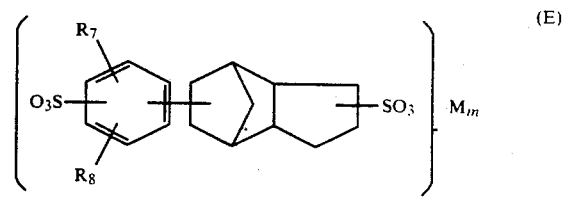
(E)

wherein $R_7$ and $R_8$, which may be the same or different, represent hydrogen atoms or alkyl groups having 1 or 2 carbon atoms; and M is the same as defined above; and m is 1 or 2 and when M is an alkaline earth metal m is 1.

(6) Condensates obtained by condensing a disulfonated dicyclopentadiene derivatives represented by the formula (E) in the presence of an aldehyde.

(7) Sulfonated dicyclopentadienes represented by the formula (F):

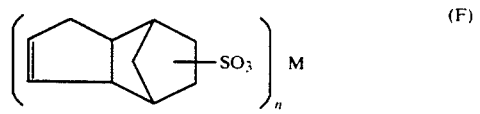
(F)

wherein M and n are the same as defined in the formula (D).

(8) Polymers or copolymers of sulfonated dicyclopentadienes represented by the formula (F).

(9) Sulfonated hydroxydicyclopentadienes represented by the formula (G):

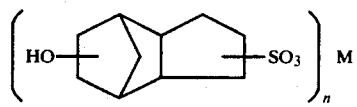

(G)

wherein M and n are the same as defined above.

(10) Polymers or copolymers of sulfonated hydroxydicyclopentadienes represented by the formula (G).

Concrete examples of cyclopentadiene derivatives represented by the formula (A) or (B) used in the above sulfonation products (1) and (2) include, for instance, cyclopentadiene; alkylcyclopentadienes such as methylcyclopentadiene, ethylcyclopentadiene, propylcyclopentadiene and the like; and dimers consisting of any combinations thereof, such as dicyclopentadiene, and the like. In this invention, these cyclopentadiene derivatives may be used alone or in combination of two or more different derivatives. Among them, cyclopentadiene, dicyclopentadiene and a mixture of the two are preferred.

The cyclopentadiene derivative used in this invention may contain impurities so long as the reaction is not hindered thereby.

Polymerizable monomers other than the cyclopentadiene derivatives may be used in the production of the aforesaid polymers in this invention (hereinafter referred to merely as "the polymerizable monomers"), and as the polymerizable monomers, there may be used hydrocarbon compounds having at least one olefinic double bond in the molecule, including aliphatic, alicyclic and aromatic ones. In order to sulfonate the portion of said polymerizable monomer in the polymers, it is necessary that at least one double bond should remain in the said portion. Therefore, the hydrocarbon compounds should preferably have at least two double bonds in the molecule, as in, for example, dienes. However, aliphatic dienes are not preferable for the purpose of increasing the strength of cement because they cause a large decrease of the surface tension of an aqueous solution of the resulting sulfonation product and also cause an increase of the air-entraining effect when used as dispersants for cement. In the case of using the polymerizable monomer, the amount thereof is such that the proportion of the cyclopentadiene derivative to the polymerizable monomer is preferably 20% by weight or more, more preferably 50% by weight or more.

An acidic compound catalyst is used in the production of the aforesaid polymers in this invention, and as the acidic compound in this case, there may be used, for example, Lewis acids or organic protonic acids such as sulfuric acid, phosphoric acid, hydrogen fluoride, boron trifluoride, boron trifluoride complexes, aluminum chloride, aluminum bromide, tin tetrachloride, zinc chloride, titanium trichloride, and the like.

In the presence of such a catalyst, the cyclopentadiene derivative is usually subjected, alone or together with the polymerizable monomer, to polymerization at a reaction temperature of −20° C. to 150° C. for several hours to obtain a polymer. In this polymerization, a polymerization solvent for allowing the reaction to proceed smoothly may be used, and as such a polymerization solvent, any solvent such as a hydrocarbon, a halogenated hydrocarbon or the like may be used so long as the polymerization is not hindered.

The number average molecular weight of the aforesaid polymer may properly be varied depending upon the reaction conditions, in particular, the kind and amount of the acidic compound catalyst and the reaction temperature, though it is preferably 200 or more when the sulfonation product of this invention is used as the dispersant for cement described below, and it is also preperable that the number average molecular weight is 10,000 or less than the viewpoint of facilitating the sulfonation of said polymers. The number average molecular weight is particularly preferably 300 to 5,000.

The number of double bonds remaining in the aforesaid polymer (hereinafter referred to merely as "the residual double bonds") can be determined by, for example, iodometry, and, in usual, they remain in a proportion of 0.3 to 1 double bond per molecule of the cyclopentadiene derivative.

For sulfonating the polymer thus obtained, there may be used the methods described in detail in E. E. Gilbert, "Sulfonation and Related Reaction", Interscience Publishers Inc. (1965), and a sulfonation method applicable to unsaturated compounds, in particular, unsaturated aliphatic or alicyclic compounds, may properly be selected depending upon the conditions of a reaction system.

The sulfonation products can also be obtained by the addition reaction of a sulfite to unsaturation shown in Charles J. Norton, "The Journal of Organic Chemistry", 4158 (1968). As the sulfonating agents, in this case, there are usually used acidic sulfites, metasulfites or sulfites of alkali metals alone or in admixture of two or more. The amount of the sulfonating agent may vary depending upon the required degree of sulfonation, and cannot unconditionally be determined, but in usual, they are used in a proportion of 0.1 to 10 molecules per one residual double bond in the polymer.

In the sulfonation, the employment of a catalyst is not always required, but in usual, the reaction time can be shortened when a catalyst such as an inorganic oxidizing agent or the like is used. As the inorganic oxidizing agent, there may be used, for example, nitrates, nitrites, chlorates and the like, and nitrates are particularly preferred.

It is preferable to use a suitable solvent in order to allow the reaction to proceed uniformly and smoothly. As said solvent, there may advantageously be used, for example, water, lower alcohols such as methyl alcohol, ethyl aclohol, propyl alcohol, isopropyl alcohol, butyl alcohol, tertiary butyl alcohol and the like, lower glycols, ketones, ethers, esters, etc. These solvents may properly be used in admixture of two or more. Among them, a mixed solvent of a lower alcohol and water, in particular, a mixed solvent of propyl alcohol and water, is recommended as an excellent solvent.

In order to dissolve the aforesaid polymer more uniformly, there may be co-used another solvent inert to the sulfonation, for example, an aromatic hydrocarbon such as benzene, toluene, xylene, ethylbenzene or the like; an aliphatic hydrocarbon such as pentane, heptane, decane or the like; or a cyclic ether such as tetrahydrofuran or the like.

The reaction temperature in the sulfonation is usually 50° to 200° C., preferably 70° to 150° C., more preferably 90° to 120° C., and the reaction can be effected either at atmospheric pressure or under pressure.

In order to suppress the progress of side reactions and inhibit the production of unnecessary inorganic salt, the pH of the reaction system is usually kept at 2 to 9, preferably 5 to 7.

The degree of condensation of the condensate obtained can properly be controlled by altering the reaction conditions such as the amount of the acid catalyst, the condensation temperature, the condensation time and the like. It is desirable to select a degree of condensation matching the application purposes. When it is used, for example, as a dispersant for cement, the number average molecular weight thereof is preferably 500 to 30,000, more preferably 800 to 10,000. The number average molecular weight can be determined by aqueous system GPC (gel permeation chromatography), and is converted by use of a calibration curve obtained by using, as standard substances, several sodium polystyrenesulfonates different in molecular weight, several sodium anthracenesulfonates different in molecular weight and several sodium benzenesulfonates different in molecular weight.

The term "condensates" used in above (4) means condensates obtained by condensing molecules of one of the sulfonated cyclopentadiene derivatives represented by the formula (D); condensates obtained by condensing different sulfonated cyclopentadiene derivatives represented by the formula (D); and condensates obtained by condensing a sulfonated cyclopentadiene derivative represented by the formula (D) with a monomer condensable therewith other than the sulfonated cyclopentadiene derivatives represented by the formula (D).

In the formula (D), when M is a hydrogen atom, an alkali metal atom, ammonium or an amine, $n=1$, and when M is an alkaline earth metal atom, $n=2$.

As the aforesaid alkali metal atom, there may be used sodium, potassium and the like. As the amine, there may be used alkylamines such as methylamine, ethylamine, propylamine, dimethylamine, diethylamine, trimethylamine, triethylamine, butylamine, dibutylamine, tributylamine, and the like; polyamines such as ethylenediamine, diethylenetriamine, triethylenetetramine and the like; morpholine; piperidine; etc. As the alkaline earth metal atom, there may be used calcium, magnesium, zinc and the like. One of the above M's may be converted into the othe M, and the latter into the former, by various ion exchange techniques or neutralization.

Each of $R_4$, $R_5$ and $R_6$ in the sulfonated cyclopentadiene derivatives represented by the formula (D) is preferably a hydrogen atom, a methyl group, a propyl group or a butyl group, and each of $R_2$ and $R_3$ is preferably a hydrogen atom.

For the production of the sulfonated cyclopentadiene derivatives represented by the formula (D), various production processes are applicable. For example, the sulfonated cyclopentadiene derivatives represented by the formula (D) can be produced by sulfonating a compound having the structural formula (H) shown below, and then, if necessary, converting it to a sulfonic acid salt:

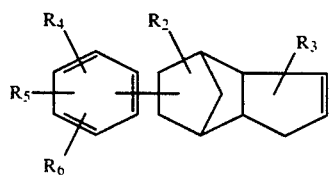
(H)

wherein $R_2$, $R_3$, $R_4$, $R_5$ and $R_6$ are the same as defined above.

The method for the sulfonation of the compound having the structural formula (H) is the same as described above as to the sulfonation products (1).

The compound having the structural formula (H) can be obtained, for example, by a Friedel-Crafts reaction of a compound represented by the structural formular (I) shown below with a compound represented by the formula (B).

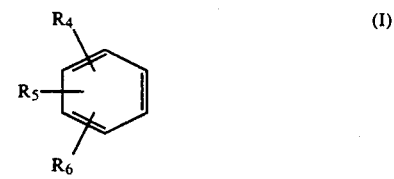
(I)

wherein $R_4$, $R_5$ and $R_6$ are the same as defined above.

As the compound represented by the structural formula (I), benzene or alkylbenzenes may be used, and as the alkylbenzens, there may be used, for example, mono-, di- or tri-alkyl-substituted benzenes such as toluene, xylene (o-, m-, p-), ethylbenzene, n-propylbenzene, iso-propylbenzene, methylethylbenzene (o-, m-, p-), 1,2,4-trimethylbenzene, n-butylbenzene, sec-butylbenzene, tert-butylbenzene, iso-propyltoluene (o-, m-, p-), amylbenzene, hexylbenzene, amyltoluene (o-, m-, p-), and the like. The alkyl groups in this case have 1 to 6 carbon atoms, and the two alkyl groups may form a ring together with the adjacent carbon atoms, an example of which is tetrahydronaphthalene. Compounds having the structural formula (I) in which $R_6$ is hydrogen are particularly preferred, and as such compounds, there may be used benzene, toluene, xylene, propylbenzene and butylbenzene.

The compound having the structural formula (B) is as defined above as to the sulfonation products (1) and (2).

As catalysts for synthesizing a compound represented by the above structural formula (H) by a Friedel-Crafts reaction of a compound represented by the above structural formula (I) with a compound represented by the formula (B), there may be used acidic compounds, for example, Lewis acids or organic protonic acids such as sulfuric acid, phosphoric acid, hydrogen fluoride, boron trifluoride, boron trifluoride complexes, aluminum chloride, aluminum bromide, tin tetrachloride, zinc chloride, titanium trichloride, and the like. The reaction is effected according to a well-known method, e.g., Japanese Patent Application Kokai (Laid-Open) No. 133,968/77. For example, the compound having the structural formula (H) can be obtained by reacting a compound having the structural formula (I) and a compound represented by the formula (B) in the presence of one of the above-mentioned catalysts for about 1 to 5 hours at a temperature of preferably 0° to 100° C., particularly preferably 20° to 70° C.

The compound represented by the structural formula (H) can also be synthesized by a Friedel-Crafts reaction of a compound having the structural formula (I) with a compound having the structural formula (J):

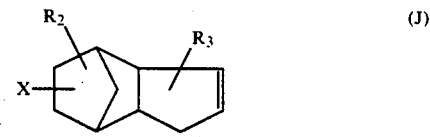
(J)

yield becomes low and when it is more than 5, side reactions such as carbonization and the like take place. The reaction time is also not critical, but in overall consideration of the reaction rate, the occurrence of side reactions and the like, it is preferably 50° to 150° C., more preferably 80° to 130° C. In order to allow the reaction to proceed smoothly, there may be used water, organic acids, organic solvents, alcohols and the like as solvents. On the other hand, when water is used as the solvent, the viscosity at the time of the reaction can be kept low, but the progress of the reaction becomes slow. Therefore, when water and a solvent showing azeotropy with water, for example, heptane, are added at the same time and the reaction is effected while removing the water, the reaction rate becomes rapid. This method is applied also when the reaction is effected while removing water in sulfuric acid.

The compounds (6) also include condensates obtained by condensing a compound of the formula (E) alone through an aldehyde and compounds obtained by condensing a compound (E) with a co-condensable compound, e.g., a benzene derivative such as benzene, toluene, xylene, phenol or the like, naphthalenesulfonic acid or its salt or the like through an aldehyde. As the condensation method, the method described in above (4) may be employed.

In the formulas (E) and (K), M is hydrogen, alkali metal, amonium, an amine, or an alkaline earth metal.

As the aforesaid alkali metal atom, there may be used sodium, potassium and the like. As the amine, there may be used alkylamines such as methylamine, triethylamine, ethylamine, propylamine, dimethylamine, diethylamine, trimethylamine triethylamine, butylamine, dibutylamine, tributylamine and the like; polyamines such as ethylenediamine, diethylenetriamine and the like; morpholine; piperidine; etc. As the alkaline earth metals, there may be used calcium, magnesium and the like. These M's are interconvertible into one another by various ion-exchange techniques.

In the case where M is Na which is one of the alkali metals, the general formula (K) is represented as follows (n is 1):

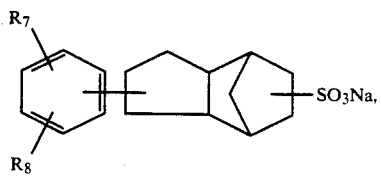

and the general formula (E) is represented as follows (m is 2):

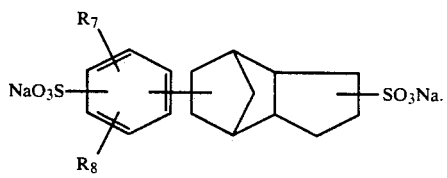

In the case where M is Ca which is one of the alkaline earth metal, the general formula (K) is represented as follows (n is 2):

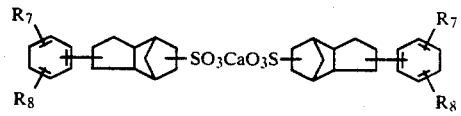

and the general formula (E) is represented as follows (m is 1):

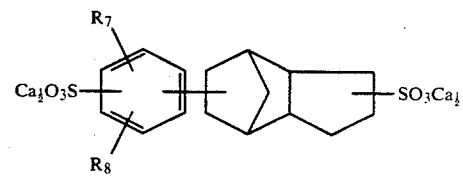

For the production of the compounds (7), various production processes are conceivable. For example, they can be produced by a process which comprises sulfonating dicyclopentadiene represented by the formula (L) shown below, and then, if necessary, converting it into a sulfonate:

As to the sulfonation applied to unsaturated compounds, in particular, unsaturated aliphatic compounds or unsaturated alicyclic compounds, the method described in above (1) is applied, and although the amount of the sulfonating agent is not critical, it is 0.1 to 2.0 moles, preferably 0.5 to 1.2 moles, more preferably 0.5 to 1.0 mole, per mole of the dicyclopentadiene. When it is less than 0.1 mole, the yield in the reaction becomes low, and when it exceeds 2.0 moles, compounds in which the double bond in the cyclopentene ring has also been sulfonated are produced in a large amount.

In the formula (F) for the compound (7), M is the same as defined in the formula (E), and the specific alkali metals, alkaline earth metals, and amines mentioned above for the formulas (E) and (K) may also be used. These M's are convertible into one another depending upon purposes by various ion-exchange techniques.

In the case where n is 1, namely M is, for example, Na which is one of the alkali metal, the general formula (F) is represented as follows:

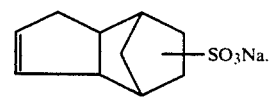

In the case where n is 2, namely M is, for example, Ca which is one of the alkaline earth metals, the general formula (F) is represented as follows:

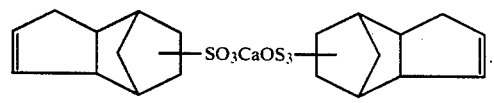

The compound (7) is usually a white to slightly yellow solid, and can be separated from the unreacted organic compounds, for example, by extraction with water. Owing to this procedure, unreacted inorganic salts present in the aqueous phase can be separated by a method such as crystallization or the like.

The sulfonation product thus obtained is a mixture of that having one sulfonic acid group per molecule and that having two sulfonic acid groups per molecule, and the proportions of these components can properly be varied depending upon the kind and amount of the sulfonating agent, the ratio of the sulfonating agent to the dicyclopentadiene, the kind and amount of the inorganic oxidizing agent or the solvent, the reaction temperature, and the like.

The sulfonated dicyclopentadienes may be any of the two kinds of sulfonation products described above. However, from the viewpoint of the facilitation of the polymerization when they are polymerized to obtain a polymer, the sulfonated dicyclopentadiene preferably has residual double bonds and it contains preferably 20% or more of that having one sulfonic acid group per molecule.

The sulfonated dicyclopentadiene contains more preferably 50% or more and most preferably 80% or more of that having one sulfonic acid group per molecule.

The number of sulfonic acid groups of the aforesaid sulfonated dicyclopentadiene can be determined by a usual method such as titration with an alkali. The salts of sulfonic acids include salts with an alkali metal such as sodium, potassium or the like; salts with an alkylamine such as methylamine, ethylamine or the like; salts with an alkaline earth metal such as calcium, magnesium or the like; and ammonium salts.

The compounds (8) are polymers or copolymers of the compounds of the formula (F), and an example of a process for producing them is shown below.

An acidic compound catalyst is used as a polymerization catalyst, and it includes, for example, Lewis acids or organic protonic acids such as sulfuric acid, phosphoric acid, hydrogen fluoride, boron trifluoride, boron trifluoride complexes, aluminum chloride, aluminum bromide, tin tetrachloride, zinc chloride, titanium trichloride, and the like.

In the presence of such a catalyst, the sulfonated dicyclopentadiene (7) alone or in admixture with a copolymerizable monomer (hereinafter referred as "the commonomer") is polymerized, in usual, at a reaction temperature of −20° to 300° C., preferably 80° to 180° C. for a period of several hours to several tens of hours to obtain a polymer. In the polymerization, a polymerization solvent may be used for effecting the reaction smoothly, and as such a polymerization solvent, there may be used a polar solvent such as water, a hydrocarbon, a halogenated hydrocarbon or the like, so long as the polymerization is not hindered.

It is also possible to control the HLB (surface active effect) by copolymerizing the sulfonation product (7) with the comonomer.

As the comonomer, there may be used, in any proportion, one or more member selected from the group consisting of aliphatic, alicyclic and aromatic hydrocarbons having an olefinic unsaturation, olefinically unsaturated amides, olefinically unsaturated alcohols, olefinically unsaturated esters, olefinically unsaturated nitriles, olefinically unsaturated carboxylic acids and esters, olefinically unsaturated sulfonic acids and esters, etc.

However, when the (co-)polymer is used as a dispersant for cement, the content of the sulfonated dicyclopentadiene in the (co-)polymer of this invention is 50% or more, preferably 70% or more, most preferably 90% or more in order to keep the air-entraining property at a low level.

The molecular weight of the (co-)polymer of the aforesaid sulfonated dicyclopentadiene can properly be controlled by selecting reaction conditions, in particular, the kind and amount of the acidic compound catalyst and the kind and amount of the solvent, the reaction temperature, or the reaction time.

When the polymers or copolymers of the aforesaid sulfonated dicyclopentadienes are used as dispersants for cement, the number average molecular weight of the polymer or copolymer is preferably 500 or more, more preferably 2,000 or more, most preferably 3,500 to 50,000.

The (co-)polymer of the aforesaid sulfonated dicyclopentadiene can be converted into the acid form, which can further be converted to the salt form with an alkali metal, an alkaline earth metal, ammonia, or an amine by an ion-exchange method, neutralization or the like.

In the compounds (9), M is as defined in the case of the compounds (5). When Na is used as the alkali metal, the compound (9) is represented by the formula:

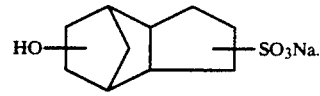

When Ca is used as the alkali metal, the compound (9) is represented by the general formula:

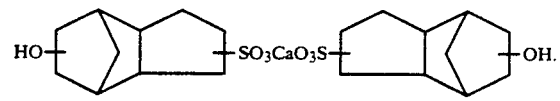

For the production of the compounds (9), various processes are conceivable. For example, they can be produced by a process which comprises sulfonating a hydroxydicyclopentadiene represented by the formula (M) shown below, and then, if necessary, converting it into a sulfonate:

(M)

As a method for sulfonating the compound (M), the method described as to the above compounds (1) is applied.

Although the amount of a sulfonating agent is not critical, it is used in an amount of, for example, 2.0 moles per mole of the hydroxydicyclopentadiene. When the amount thereof is less than 0.1 mole, the yield in the reaction becomes low, and therefore, in usual, the sulfonating agent is preferably used in an amount of 0.5 mole or more.

The compound (9) is usually a white to slightly yellow solid and the M's are convertible into one another by various ion-exchange techniques.

The compounds (10) are polymers or copolymers of the compounds of the formula (G). An example of a process for producing them is shown below. An acidic compound catalyst is used as the polymerization catalyst, and as this catalyst, there may be used, for instant, Lewis acids or organic protonic acids such as sulfuric acid, phosphoric acid, hydrogen fluoride, boron trifluoride, boron trifluoride complexes, aluminum chloride, aluminum bromide, tin tetrachloride, zinc chloride, titanium trichloride, and the like.

In the presence of such a catalyst, the sulfonated hydroxydicyclopentadiene is polymerized alone or in admixture with the comonomer, in usual, at a reaction temperature of −20° to 300° C., preferably 80° to 180° C. for a period of several hours to several tens of hours to obtain a polymer. In the polymerization, a polymerization solvent may be used for effecting the reaction smoothly, and as such a polymerization solvent, there may be used a polar solvent such as water, a hydrocarbon, a halogenated hydrocarbon or the like, so long as the polymerization is not hindered.

It is also possible to control the HLB (surface active effect) by copolymerizing the sulfonation product of this invention with the comonomer. Specific examples of the comonomer are as mentioned hereinbefore.

The molecular weight of the (co-)polymer of the aforesaid sulfonation product can properly be controlled by selecting reaction conditions, in particular, the kind and amount of the acidic compound catalyst and the kind and amount of the solvent, the reaction temperature, or the reaction time.

When the (co-)polymer of the sulfonation product of this invention is used as a dispersant for cement, the number average molecular weight of the (co-)polymer is preferably 500 or more, more preferably 2,000 or more, most preferably 3,500 to 50,000.

The (co-)polymer of the sulfonated product of this invention can be converted into the acid form which can further be converted to the salt form with an alkali metal, an alkaline earth metal, ammonia, or an amine by an ion-exchange method, neutralization or the like.

Since the compounds (1), (2), (3), (4), (5), (6), (7), (8), (9) and (10) of this invention have an excellent surface active effect, they are very useful as surfactants for organic materials or inorganic materials, and are used as, for example, emulsifiers, dispersants, wetting agents, detergents and smoothing agents or as intermediates for synthesizing the compounds (7) and (9). They are particularly useful as dispersants for cement, and in this case, the dispersibility of cement in water can greatly be improved, so that the amount of water can be decreased in a cement construction method.

This invention relates also to a slurry composition comprising a powder, a dispersant having at least one sulfonic acid group and a polymer emulsion.

In general, dispersants are used for dispersing a powder of cement, gypsum, pigment, dye or the like in a medium such as water or the like. Particularly, in the case of cement paste it has strongly been desired that the hardened cement does not have cracks and has a high strength. Therefore, attempts have been made to make the amount of water in the cement paste as small as possible. However, when the proportion of water in the cement paste is simply made small, the fluidity of the cement paste is lowered, so that the desired cement construction cannot be carried out. Therefore, an attempt has been made to add a dispersant to reduce the proportion of water and simultaneously attain a high fluidity. The dispersant includes those of naphthalene type, triazine type, lignin type, polyol type, oxycarboxylic acid type and the like, and these compounds are used alone or in combination of two or more. However, when the said dispersants are added, the resulting cement paste has a high fluidity at the beginning of the addition, but shows such phenomena that the slump loss is great and the fluidity decreases in a very short time. This is a serious disadvantage in cement construction method.

In view of the situation described above, the present inventors have conducted extensive research to find that the addition of a polymer emulsion together with a dispersant having at least one sulfonic acid group to cement improves the dispersing effect of the dispersant, further enhances the fluidizing effect of the dispersant, and makes the slump loss very small and the workability good, and also find that an excellent dispersibility can be obtained also when a dispersant having at least one sulfonic acid group and the aforesaid polymer emulsion are added to a powder other than cement, for example, gypsum, pigment, dye, etc.

An object of this invention is to provide a slurry composition having an excellent dispersability.

Another object of this invention is to provide a slurry composition comprising cement as powder, which can give a cement paste having a high fluidity, showing only a small slump loss, and a low entrainability.

According to this invention, there is provided a slurry composition characterized by comprising a powder, a dispersant having at least one sulfonic acid group, and a polymer emulsion, the polymer emulsion being present in a proportion of 0.05 to 50 parts by weight in terms of solids per 100 parts by weight of said dispersant.

The slurry composition of this invention may contain additives properly added depending on the kind of the powder.

In this invention, as the powder, there may be used cement, gypsum, a pigment, a dye or the like. Among them, as the cement, there may be used, for example, various portland cements such as normal portland cement, high early strength portland cement, ultra-high early strength portland cement, moderate heat portland cement, sulfate-resistant portland cement, white iron portland cement and the like; well-known cements such as blast furnace cement, portland pozzolan cement, fly ash cement, aluminous cement, solidit, calcium silicate and the like; mixed cements obtained by combining two or more of them; and mixed cement of these cements and inorganic materials such as gypsum and the like. There may be used mortar obtained by adding sand to these cements, concrete obtained by further adding gravel to the mortor, etc. There may also be added, depending on purposes, various additives conventionally used as compounding agents for cement, for example, air-entraining agents, accelerating agents, retarding agents, water-proofing agents and the like in any combination. As the dispersant having at least one sulfonic acid group, there may be used, for example, conventional dispersants, e.g., those commercially available as dispersants, such as condensates of naphthalenesulfonates, condensates of triazinesulfonates, condensates of alkylallylsulfonates, condensates of anthracenesulfonates, lignin sulfonates, co-condensates of lignin and naphthalenesulfonates, and the like, and those obtained by modifying these dispersants; sulfonation products obtained by sulfonating a reaction mixture prepared by reacting a cyclopentadiene derivative represented by the formula (A) and (B) shown below with a compound represented by the formula (C) shown below; condensation products obtained by condensing the sulfonation mixture through an aldehyde or the like; sulfonation products obtained by sulfonating a polymer prepared by polymerizing a cyclopentadiene derivative represented, for example, by the formula (A) or (B) shown below; sulfonation products of cyclopentadiene derivatives represented by the formula (D) shown below or condensates obtained by condensing these sulfonation products through an aldehyde; sulfonation products of dicyclopentadienes represented by the formula (E) or (co-)polymers thereof; and sulfonation products of hydroxydicyclopentadienes represented by the formula (F) or (co-)polymers thereof:

 (A)

wherein $R_1$ is a hydrogen atom or an alkyl group having 1 to 3 carbon atoms,

 (B)

wherein $R_2$ and $R_3$, which may be identical or different, are hydrogen atoms or alkyl groups having 1 to 3 carbon atoms,

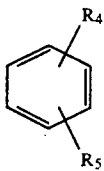 (C)

wherein $R_4$ and $R_5$, which may be identical or different, are hydrogen atoms or alkyl groups having 1 to 6 carbon atoms,

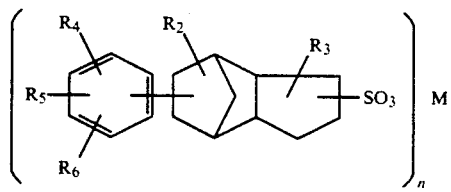 (D)

wherein $R_2$, $R_3$, $R_4$ and $R_5$ are the same as defined above; $R_6$ is a hydrogen atom or an alkyl group having 1 to 6 carbon atoms; $R_4$, $R_5$ and $R_6$ may be identical with or different from one another; M is hydrogen, an alkali metal, an alkaline earth metal, ammonium or an amine; and n is 1 or 2 and when M is an alkaline earth metal n is 2,

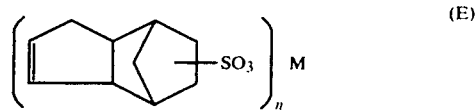 (E)

wherein M and n are the same as defined above,

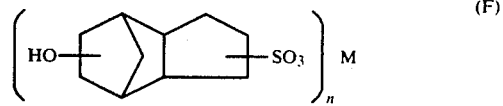 (F)

wherein M and n are the same as defined above.

These dispersants may be used alone or in combination of two or more, and it is also possible to use the dispersants having at least one sulfonic acid group in combination with dispersants free from sulfonic acid group. The proportion of the dispersant having at least one sulfonic acid group used may be varied depending on the kind of the powder. When the powder is particularly a cement, the proportion of said dispersant to the cement cannot unconditionally be defined because it is determined collectively considering compounding conditions such as the kind and proportion of the cement, the kind and proportion of an aggregate if added, and the like, and physical properties such as the required fluidity and the strength of the cement after hardening, but in general, it is preferable that the dispersant is used in a proportion of 0.01 to 10 parts by weight per 100 parts by weight of the cement.

Although the polymer emulsion used in this invention is not critical, it is preferably a polymer emulsion obtained by subjecting polymerizable monomers alone or in combination of two or more to emulsion polymerization or suspension polymerization in an aqueous medium in the presence of a radical polymerization initiator. However there may satisfactorily be used a polymer emulsion obtained by the so-called re-emulsification method by which a solution prepared by dissolving a solid polymer obtained, for example, by solution polymerization, in a hydrophobic solvent is dispersed and emulsified in an aqueous medium with or without an emulsifier, and thereafter the hydrophobic solvent is removed.

As the monomers used for preparing the polymer in such a polymer emulsion, the following are representatives, though other monomers than the following may also be appropriately used: aromatic alkenyl compounds such as styrene, α-methylstyrene, monochlorostyrene, vinyltoluene, methoxystyrene and the like; ethylenically unsaturated monocarboxylic acids such as acrylic acid, methacrylic acid, crotonic acid and the like; ethylenically unsaturated dicarboxylic acids such as itaconic acid, fumaric acid, maleic acid and the like; ethylenically unsaturated monocarboxylic acid esters such as methyl acrylate, ethyl acrylate, propyl acrylate, butyl acrylate, lauryl acrylate, methyl methacrylate, ethyl methacrylate, propyl methacrylate, butyl methacrylate, hydroxyethyl acrylate, hydroxypropyl acrylate, hydroxyethyl methacrylate and the like; ethylenically unsaturated dicarboxylic acid esters such as dimethyl itaconate, dimethyl maleate, and the like; alkenyl cyanides such as acrylonitrile, methacrylonitrile and the like; conjugated dienes such as butadiene, isoprene, piperylene, chloroprene, butadienyl acetate and the like; vinyl chloride; vinylidene chloride; vinyl methyl ketone; vinyl methyl ether; vinyl acetate; vinyl formate; allyl acetate; methallyl acetate; acrylamide; methacrylamide; N-methylolacrylamine; vinylpyridine; glycidyl acrylate; glycidyl methacrylate; acrolein; allyl alcohol; and the like.

When the aforesaid polymer emulsion is produced by emulsion polymerization or suspension polymerization, the polymerization temperature is usually $-10°$ C. to $100°$ C., and either batch polymerization, semibatch polymerization or continuous polymerization may be effected. In such polymerization, polymerization initiators, chain transfer agents, emulsifiers and the like may appropriately be used, and depending on the like of the monomer, it is also possible to obtain a polymer emulsion by effecting the polymerization without any emulsifier.

As the polymerization initiators used for producing the aforesaid polymer emulsion by emulsion polymerization or suspension polymerization, there may be used water-soluble initiators such as potassium persulfate, ammonium persulfate and the like; oil-soluble initiators such as benzoyl peroxide and the like; redox initiators; etc. As the chain transfer agents, there may be used tert-dodecylmercaptan, carbon tetrachloride and the like which are usually used. Further, when the aforesaid polymer emulsion is produced by emulsion polymerization, the polymerization may be effected by adding polymerization adjuvants such as chelating agents, inorganic salts and the like which are used in the conventional emulsion polymerization.

As the emulsifiers used for producing the aforesaid polymer emulsion by emulsion polymerization or by a re-emulsification method, there may be used anionic surfactants and nonionic surfactants alone or in a proper combination. As the anionic surfactants, there may be used, for example, sulfuric esters of higher alcohols, alkylbenzenesulfonates, aliphatic sulfonates and the like, and as the nonionic surfactants, there may be used, for example, alkyl ester forms, alkyl ether forms and alkyl phenyl ether forms of polyethylene glycol, and the like. It is also possible to use polyvinyl alcohol or the like as an emulsification stabilizer together with these emulsifiers.

Particularly preferred in this invention are the following two groups of emulsions:

(1) Polymer emulsions obtained by subjecting a polymerizable monomer to emulsion polymerization or suspension polymerization in an aqueous medium containing one or more surfactants in an amount of 0 to 1 part by weight per 100 parts by weight of said polymerizable monomer.

As surfactants usable for producing the aforesaid polymer emulsions (1), those conventionally used in emulsion polymerization may be used, and among them, preferable are anionic surfactants such as sulfuric ester of higher alcohols, alkylbenzenesulfonates, aliphatic sulfonates and the like, and nonionic surfactants such as alkyl ester forms, alkyl ether forms and alkyl phenyl ether forms of polyethylene glycol, and the like.

Such surfactants may be used alone or in combination of two or more, and the proportion thereof is 0 to 1 part by weight, preferably 0 to 0.5 part by weight, and more preferably 0 to 0.2 part by weight, per 100 parts by weight of the polymerizable monomer. Said proportion is most preferably 0 part by weight so long as the polymer emulsions are satisfactorily produced. When it exceeds 1 part by weight, the resulting slurry composition foams greatly and the workability is deteriorated. That is to say, in order to inhibit the slurry composition from foaming it is ideal to use no surfactant in the production of the polymer emulsions.

As the polymerizable monomer used for producing the polymer in the polymer emulsions (1), those described above may be exemplified as representatives.

(2) Polymer emulsions obtained by subjecting a polymerizable monomer mixture comprising at least one acrylic acid ester, at least one ethylenically unsaturated carboxylic acid, and, if necessary, at least one polymerizable monomer other than the aforesaid acrylic ester and ethylenically unsaturated carboxylic acid (hereinafter referred to merely as "the other monomer") added thereto, to emulsion polymerization or suspension polymerization, for example, in an aqueous medium in the presence of a radical polymerization initiator. There may also satisfactorily be used polymer emulsions obtained by a so-called re-emulsification method by which a solution prepared by dissolving, in a hydrophobic solvent, a solid polymer obtained by polymerizing a polymerizable monomer mixture comprising at least one acrylic ester, at least one ethylenically unsaturated carboxylic acid, and, if necessary, the other monomer added thereto by solution polymerization or the like is dispersed and emulsified in an aqueous medium with or without an emulsifier, and thereafter, the hydrophobic solvent is removed.

As the acrylic ester used for producing the polymer in the aforesaid polymer emulsions (2), preferred are alkyl acrylate or hydroxyalkyl acrylate, the alkyl group of which is of a straight-chain or branched chain and has 1 to 12 carbon atoms, and there may be used, for example, methyl acrylate, ethyl acrylate, propyl acrylate, butyl acrylate, lauryl acrylate, hydroxyethyl acrylate, hydroxypropyl acrylate, and the like. These may be used alone or in combination of two or more. The proportion of the acrylate in the polymerizable monomer mixture is preferably 10 to 99.9% by weight, more preferably 30 to 99.9% by weight, and most preferably 70 to 99.9% by weight in order to obtain the effect of this invention sufficiently.

As the ethylenically unsaturated carboxylic acid used for producing the polymer in the aforesaid polymer emulsions (2), there may be used, for example, unsaturated monocarboxylic acids such as acrylic acid, methacrylic acid, crotonic acid and the like; unsaturated dicarboxylic acids such as itaconic acid, fumaric acid, maleic acid and the like; and monoesters of said unsaturated dicarboxylic acids. These may be used alone or in combination of two or more. The proportion of such ethylenically unsaturated carboxylic acids in the polymerizable monomer mixture is preferably 0.1 to 20% by weight, more preferably 0.3 to 10% by weight, and most preferably 0.5 to 7% by weight in order to obtain the effect of this invention sufficiently.

As the other monomer usable for producing the polymer in the aforesaid polymer emulsions (2), the above-mentioned polymerizable monomers other than the acrylic esters and ethylenically unsaturated carboxylic acids are representatives.

As the emulsifier used for producing the aforesaid polymer emulsions (2) by emulsion polymerization or a re-emulsification method, anionic surfactants or nonionic surfactants may be used alone or in a proper combination. As the anionic surfactants, there may be used, for example, sulfuric esters of higher alcohols, alkylbenzenesulfonates, aliphatic sulfonates and the like, and as the nonionic surfactants, there may be used, for example, alkyl ester forms, alkyl ether forms and alkyl phenyl ether forms of polyethylene glycol, and the like. Such surfactants may be used alone or in combination of two or more, and the proportion thereof is 0 to 1 part by weight, preferably 0 to 0.5 part by weight, more preferably 0 to 0.2 part by weight, per 100 parts by weight of the polymerizable monomer mixture. It is most preferably 0 part by weight per 100 parts by weight of the polymerizable monomer mixture, so long as the polymer emulsions are satisfactorily produced. When it exceeds 1 part by weight, the resulting slurry composition foams greatly. Therefore, it is not desirable.

In this invention, the polymer emulsions obtained in the manner described above may be used alone or in a proper combination of two or more.

In this invention, the amount of the abovementioned polymer emulsion used is 0.05 to 50 parts by weight, preferably 0.1 to 30 parts by weight (as solids) per 100 parts by weight of the dispersant containing at least one sulfonic acid group. When it is less than 0.05 part by weight or more than 50 parts by weight, no effect can be obtained.

In this invention, there may be used a method comprising previously mixing a dispersant having at least one sulfonic acid group with a polymer emulsion and adding the resulting mixture to a powder, or a method comprising separately adding said dispersant and said polymer emulsion to the powder.

In the slurry composition of this invention, the dispersing effect of the dispersant is very great, a powder such as cement, gypsum, a pigment, a dye or the like is uniformly dispersed, and the durability of said effect is high. Particularly when the powder is cement, the dispersing effect of the dispersant is much greater, so that the fluidity of the resulting cement paste becomes very high, and only a very small slump loss is caused, and hence, the high fluidity is maintained for a long time. Further, air bubbles are hardly entrained, so that hardened cement having a high strength can be obtained, and therefore, a cement construction method can advantageously be carried out.

Figure 2:
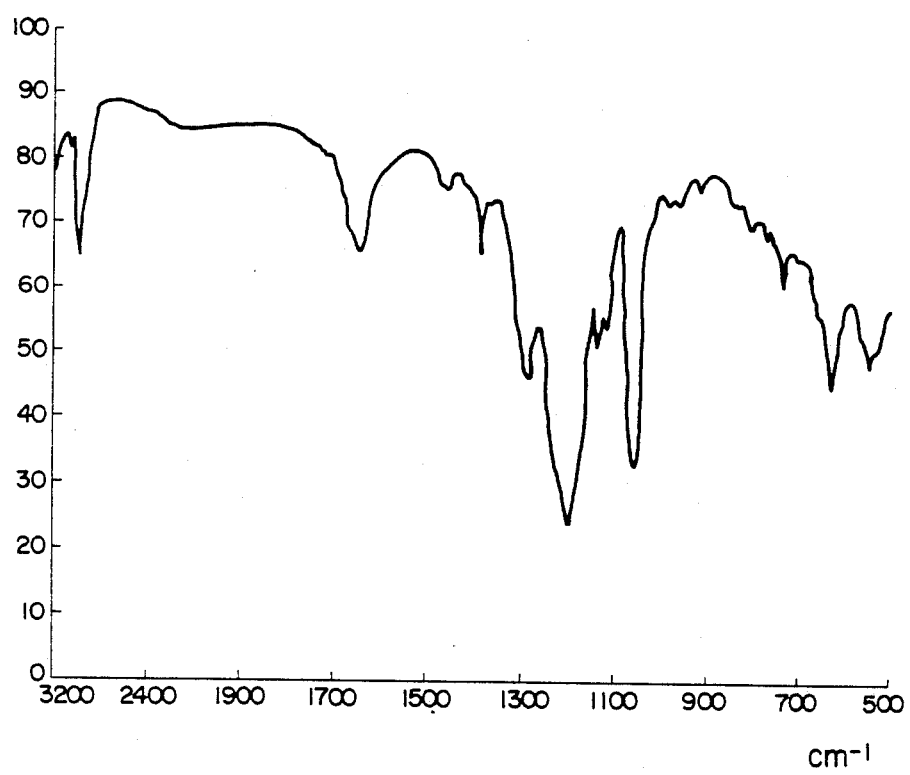
Figure 3:
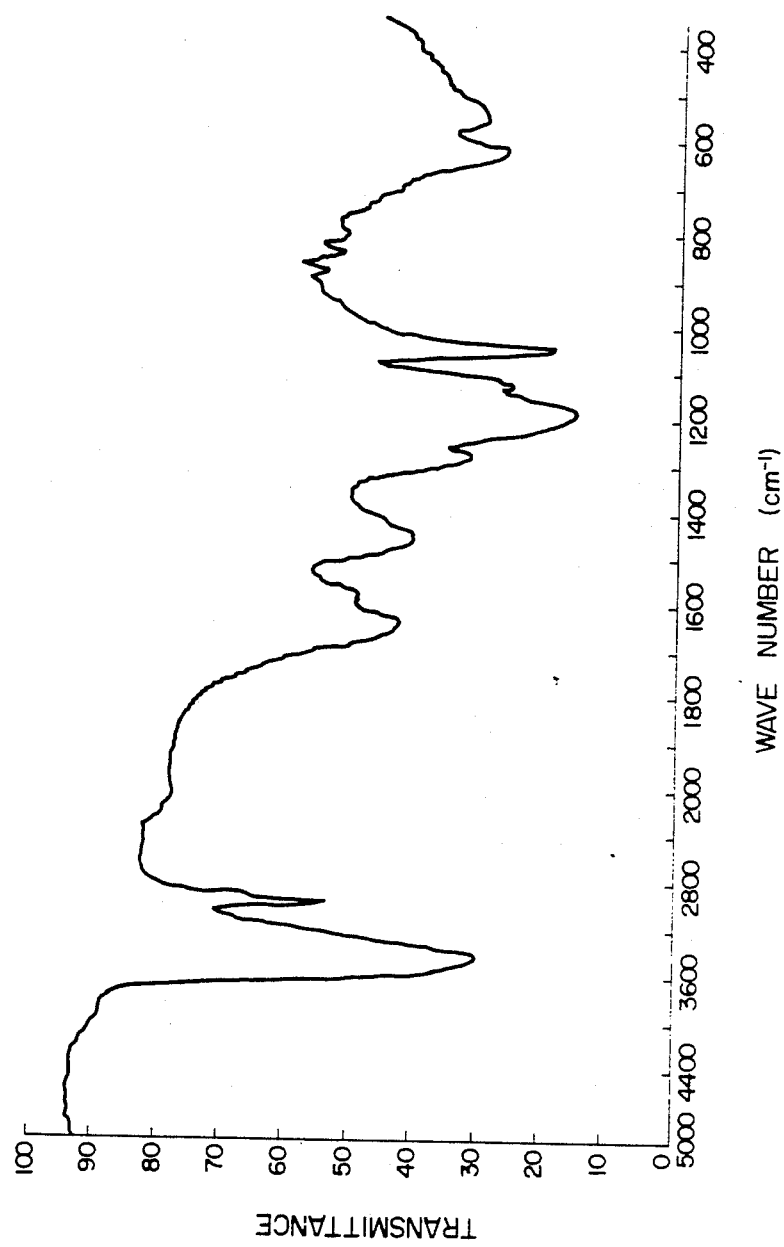
Figure 4:
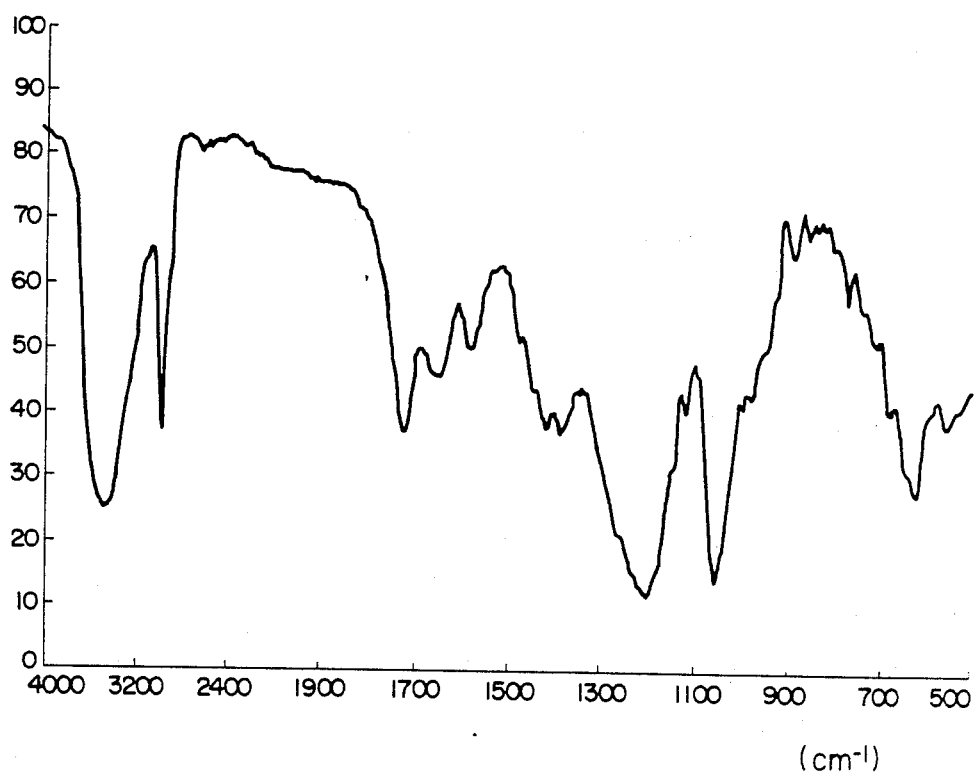
Figure 5:
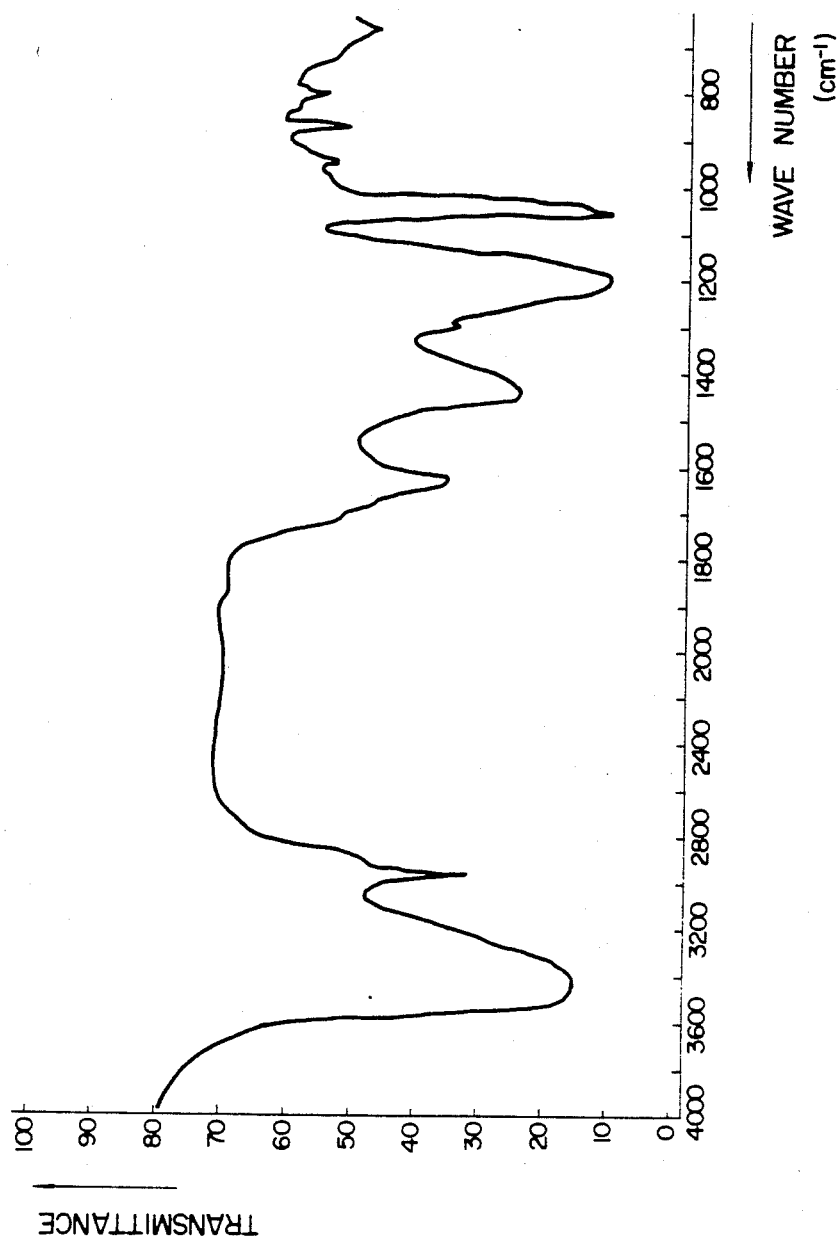
Figure 6:
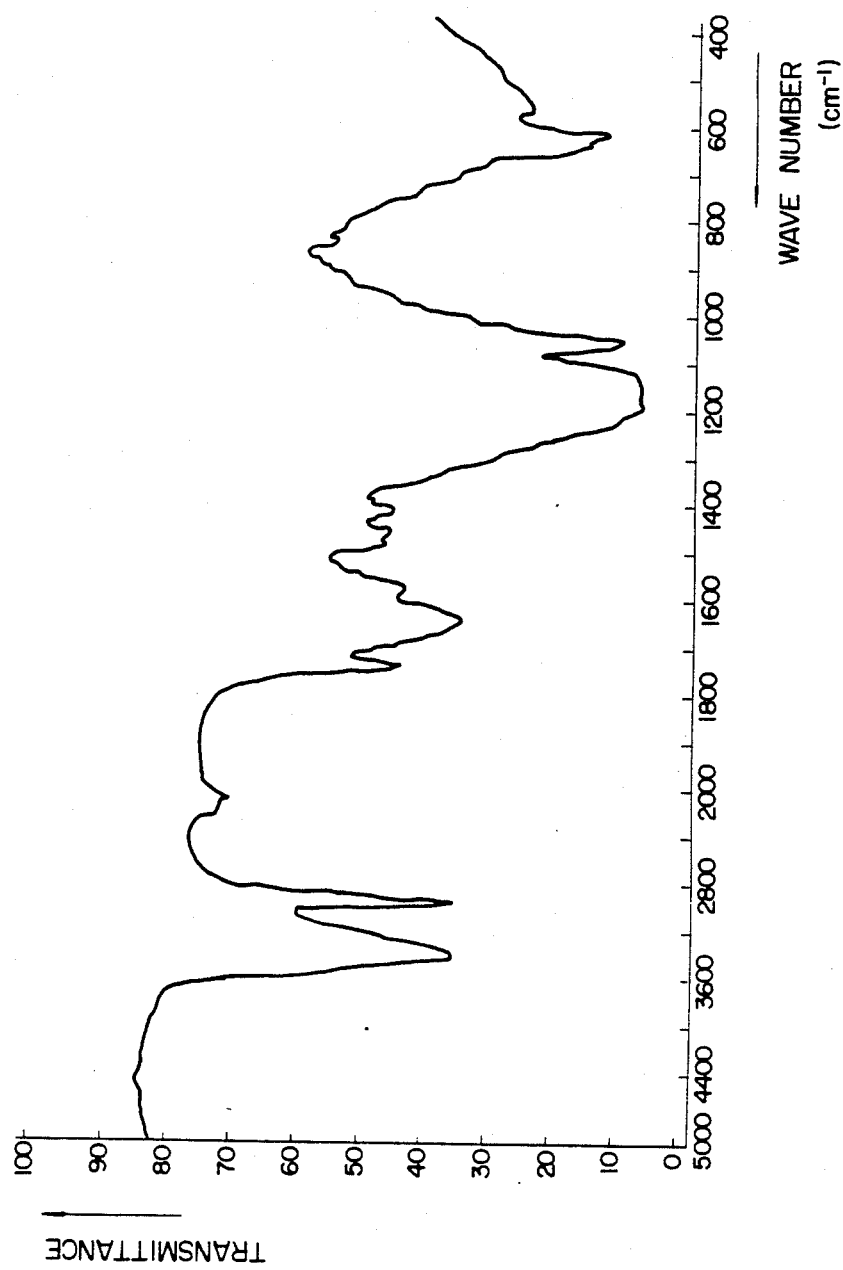

This invention is further explained below referring to Examples and the accompanying drawings, in which FIG. 1 shows an infrared absorption spectrum of the condensate of this invention obtained in Example 12, FIG. 2 shows an infrared absorption spectrum of the sulfonation product obtained in Example 22, FIG. 3 shows an infrared absorption spectrum of the polymer obtained in Example 23, FIG. 4 shows an infrared absorption spectrum of the sulfonation product obtained in Example 28, FIG. 5 shows an infrared absorption spectrum of the sulfonation product obtained in Example 29, and FIG. 6 shows an infrared absorption spectrum of the sulfonation product obtained in Example 35. This invention should not be understood to be limited to the Examples.

The number average molecular weights described in Examples 1, 2, 3, 4, 6, 7 and 8 are obtained by converting the results of measurement by GPC (gel permeation chromatography), by use of a calibration curve obtained by using several polystyrenes different in molecular weight as standard substances.

EXAMPLE 1

In a 1-liter, three-necked flask equipped with a reflux condenser and a stirrer were placed 400 g of n-hexane and 4 g of a boron trifluoride-phenol complex, and heated to a temperature of 50° C., after which 140 g of dicyclopentadiene having a purity of 95% was added dropwise with stirring over a period of about 1 hour, and the resulting mixture was further subjected to reaction at said temperature for 2 hours. After completion of the reaction, the catalyst was decomposed with an aqueous sodium carbonate solution, and the reaction mixture was washed with water, after which the oil layer was distilled under reduced pressure to remove n-hexane and unreacted dicyclopentadiene. The weight of the resulting residue was 78 g, and the number average molecular weight of the residue was 2,100. The amount of the residual double bonds in the residue was determined by iodometry to find that it was 0.83 equivalent per mole of the reacted dicyclopentadiene.

Subsequently, 20 g of the aforesaid residue, 30 g of toluene, 20 g of sodium hydrogensulfite, 2 g of potassium nitrate, 300 ml of isopropyl alcohol and 50 g of distilled water were placed in a 1-liter, stainless steel autoclave equipped with a stirrer and a thermometer, and air was supplied until the internal pressure in the autoclave became 1.0 $Kg/cm^2$ (gauge pressure) at room temperature. Then, the valve was locked up, and the mixture thus obtained was subjected to reaction at a temperature of 110° C. for 5 hours while vigorously stirring the mixture. Thereafter, the reaction mixture was allowed to stand at room temperature, and the major part of the isopropyl alcohol was removed by distillation, after which 1 liter of distilled water and 1.5 liters of petroleum ether were added, and the resulting mixture was sufficiently stirred. The separated petroleum ether layer and the precipitates were removed, and the aqueous layer thus obtained was concentrated to dryness. The concentrate was then dissolved in glacial acetic acid, and an acetic acid-insoluble fraction consisting of an inorganic salt was removed by filtration. The acetic acid-soluble fraction thus obtained was concentrated, to obtain 18.7 g of a whitish-yellow solid. This solid is named "Sample 1".

An aqueous solution of Sample 1 was converted into the acid form by means of an ion-exchange resin and titrated with sodium hydroxide to find that about 78% of the residual double bonds in the residue had been sulfonated. The solubility in water of Sample 1 was 30% by weight or more. Water was added to Sample 1 so as to prepare a 4% by weight aqueous solution, and its surface tension at a temperature of 25° C. was measured to find that it was 54.2 dyn/cm.

EXAMPLE 2

The same treatment as in Example 1 was repeated, except that the reaction was effected at 65° C., to obtain 96 g of a residue. The number average molecular weight of the residue was 530. The amount of the residual double bonds in the residue was determined in the same manner as in Example 1 to find that it was 0.76 equivalent per mole of the reacted dicyclopentadiene.

Subsequently, sulfonation treatment was carried out in the same manner as in Example 1 to obtain 27.3 g of a whitish-yellow solid. This solid is named "Sample 2".

An aqueous solution of Sample 2 was converted into the acid form by means of an ion-exchange resin and titrated with sodium hydroxide to find that about 96% of the residual double bonds in the residue had been sulfonated. The solubility in water of Sample 2 was 40% by weight or more. Water was added to Sample 2 so as to prepre a 4% by weight aqueous solution and its surface tension at a temperature of 25° C. was measured to find that it was 51.3 dyn/cm.

EXAMPLE 3

The same treatment as in Example 1 was repeated, except that cyclopentadiene was substituted for the dicyclopentadiene and the reaction was effected at a temperature of 30° C., to obtain 68 g of a residue. The number average molecular weight of the residue was 5,600. The amount of residual double bonds in the residue was determined in the same manner as in Example 1 to find that it was 0.90 equivalent per mole of the reacted cyclopentadiene.

Subsequently, sulfonation treatment was carried out in the same manner as in Example 1 to obtain 14.3 g of a whitish-yellow solid. This solid is named "Sample 3".

An aqueous solution of Sample 3 was converted into the acid form by means of an ion-exchange resin and titrated with sodium hydroxide to find that about 67% of the double bonds in the residue had been sulfonated. The solubility in water of Sample 3 was 20% by weight or more. Water was added to Sample 3 so as to prepare a 4% by weight aqueous solution, and its surface tension at a temperature of 25° C. was measured to find that it was 52.3 dyn/cm.

EXAMPLE 4

The same reaction as in Example 1 was repeated, except that the amount of dicyclopentadiene was changed from 140 g to 100 g and that 40 g of 1,3-pentadiene having a purity of 70% was newly added and reacted, to obtain 63 g of a residue. The number average molecular weight of the residue was 2,300. The amount of residual double bonds in the residue were determined in the same manner as in Example 1 to find that it was 0.87 equivalent per mole of the total of the reacted dicyclopentadiene and 1,3-pentadiene.

Subsequently, sulfonation treatment was carried out in the same manner as in Example 1, to obtain 17.6 g of a whitish-yellow solid. This solid is named "Sample 4".

An aqueous solution of Sample 4 was converted into the acid form by means of an ion-exchange resin and titrated with sodium hydroxide to find that about 81% of the residual double bonds in the residue had been sulfonated. The solubility in water of Sample 4 was 30% by weight or more. Water was added to Sample 4 so as to prepare a 4% by weight aqueous solution, and the surface tension thereof at a temperature of 25° C. was measured to find that it was 49.3 dyn/cm.

EXAMPLE 5

In 50 g of distilled water was dissolved 2 g of each of Samples 1 to 4 obtained in Examples 1 to 4, whereby four, in total, aqueous solutions were prepared. To each of the aqueous solutions was added 200 g of commercially available portland cement (manufactured by Chichibu Cement Co., Ltd.), and the mixture thus obtained were individually kneaded by hand for 3 minutes, after which the flow values were determined by use of a flow corn with an inner volume of 98.9 cc according to JIS R5201, to obtain the results shown in Table 1.

TABLE 1

| | Flow value (mm) |
|---|---|
| Sample 1 | 157 |
| Sample 2 | 138 |
| Sample 3 | 147 |

TABLE 1-continued

| | Flow value (mm) |
|---|---|
| Sample 4 | 150 |

On the other hand, when the same treatment as described above was repeated, except that none of Samples 1 to 4 were added, the flow value was only 87 mm.

As can be understood from Examples 1 to 4, the compounds (1) readily cause foaming and have an excellent surface active effect, and as can be seen from Example 5, when they are used as dispersants for cement, they have a very great and excellent effect on dispersing cement in water.

EXAMPLE 6

In a 3-liter, three-necked flask equipped with a reflux condenser and a stirrer were placed 1,270 g of toluene and 12 g of a boron trifluoride-phenol complex, and heated to 50° C., after which a mixed solution of 417 g of dicyclopentadiene and 320 g of toluene was dropped thereinto with stirring over a period of about 1 hour, and the resulting mixture was furhter subjected to reaction at said temperature for 2 hours. After completion of the reaction, the catalyst was decomposed with a sodium carbonate solution, and the reaction mixture was washed with water, after which the oil layer was distilled under reduced pressure to obtain remove 1,360 g of unreacted toluene and 35 of unreacted dicyclopentadiene, whereby 601 g of a residue was obtained. The amount of the residual double bonds in the residue was determined by iodometry to find that it was 0.96 equivalent per mole of the reacted dicyclopentadiene. The molecular weight distribution of the residue was investigated by GPC to find that there existed compounds having various molecular weights ranging from the lower limit 224, which is the molecular weight of a compound (about 63% by weight) formed by the addition of 1 mole of toluene to 1 mole of dicyclopentadiene, to a molecular weight of 8,000 (polystyrene-reduced molecular weight).

Subsequently, 20 g of the above-mentioned residue, 20 g of sodium hydrogensulfite, 2 g of potassium nitrate, 300 ml of isopropyl alcohol and 50 g of distilled water were placed in a 3-liter, stainless steel autoclave equipped with a stirrer and a thermometer, and air was supplied until the internal pressure in the autoclave became 1.0 kg/cm$^2$ (gauge pressure) at room temperature, after which the valve was locked up, and the mixture thus obtained was subjected to reaction at 110° C. for 3 hours while strongly stirring the mixture. Thereafter, the reaction mixture was allowed to stand at room temperature, and the major part of the isopropyl alcohol was removed by distillation, after which 1 liter of distilled water and 1.5 liters of petroleum ether were added. The resulting mixture was sufficiently stirred. The separated petroleum ether layer and the precipitates were removed, and the aqueous layer thus obtained was concentrated to dryness. The concentrate was then dissolved in glacial acetic acid, and an acetic acid-insoluble fraction consisting of inorganic salts was removed by filtration. The acetic acid-soluble fraction thus obtained was concentrated, to obtain 25.8 g of a yellow solid. This solid is named "Sample 5".

Sample 5 was dissolved in distilled water, converted into the acid form by means of an ion-exchange resin, and then titrated with sodium hydroxide to find that about 96% of the residual double bonds had been sulfonated. The solubility in water of Sample 5 was 40% by weight or more. Water was added to Sample 5 so as to prepare a 4% by weight aqueous solution, and the surface tension thereof was measured to find that it was 48.9 dyn/cm.

EXAMPLE 7

The same reaction as in Example 6 was repeated, except that 1,510 g of ethylbenzene was substituted for the 1,270 g of initially charged toluene and that 320 g of ethylbenzene was substituted for the 320 g of dropped toluene. Then, 1,590 g of unreacted ethylbenzene and 52 g of unreacted dicyclopentadiene were removed by distillation to obtain 588 g of a residue. The amount of the residual double bonds in the residue was determined by iodometry to find that it was 0.95 equivalent per mole of the reacted dicyclopentadiene. The molecular weight distribution of the residue was investigated in the same manner as in Example 6 to find that there existed compounds having various molecular weights ranging from the lower limit 238, which is the molecular weight of a compound (about 58% by weight) formed by the addition of 1 mole of ethylbenzene to 1 mole of dicyclopentadiene, to a molecular weight of 11,000 (polystyrene-reduced molecular weight).

Subsequently, sulfonation treatment was carried out in the same manner as in Example 6 to obtain 23.8 g of a yellow solid. This solid is named "Sample 6".

Sample 6 was dissolved in water, converted into the acid form by means of an ion-exchange resin, and then titrated with sodium hydroxide to find that about 92% of the residual double bonds had been sulfonated. The solubility in water of Sample 6 was 30% by weight or more. Water was added to Sample 6 so as to prepare a 4% by weight aqueous solution, and the surface tension thereof was measured to find that it was 47.3 dyn/cm.

EXAMPLE 8

The same reaction as in Example 6 was repeated, except that 1,510 g of xylene was substituted for the 1,270 g of initially charged toluene and that a mixed solution of 300 g of dicyclopentadiene, 320 g of xylene and 100 g of piperylene having a purity of 70% was dropped. Then, 1,560 g of unreacted xylene, 33 g of unreacted dicyclopentadiene and 48 g of unreacted piperylene were removed by distillation to obtain 563 g of a residue. The amount of the residual double bonds in the residue was determined by iodometry to find that it was 0.92 mole per mole of the reacted dicyclopentadiene. The molecular weight distribution of the residue was investigated in the same manner as in Example 6 to find that there existed compounds having various molecular weights ranging from the lower limit 238, which is the molecular weight of a compound (about 61% by weight) formed by the addition of 1 mole of xylene to 1 mole of dicyclopentadiene, to a molecular weight of 10,500 (polystyrene-reduced molecular weight).

Subsequently, sulfonation treatment was carried out in the same manner as in Example 6 to obtain 22.9 g of a yellow solid. This solid is named "Sample 7".

Sample 7 was dissolved in distilled water, converted into the aicd form by means of an ion-exchange resin, and then titrated with sodium hydroxide to find that about 94% of the residual double bonds in the residue had been sulfonated. The solubility in water of Sample 7 was 30% by weight or more. Water was added to Sample 7 to prepare a 4% by weight aqueous solution, and the surface tension thereof was measured to find that it was 43.8 dyn/cm.

EXAMPLE 9

Into a 0.2-liter, three-necked flask equipped with a stirrer and a thermometer were charged 30 millimoles of Sample 5 obtained in Example 6, 30 millimoles of formaldehyde, 30 millimoles of sulfuric acid and 270 millimoles of distilled water, and subjected to condensation at 80° C. for 24 hours. After 100 g of distilled water was added to the resulting reaction mixture, calcium carbonate was added thereto with stirring until the pH became 7, and the resulting mixture was filtered to obtain a filtrate. Further, sodium carbonate was added to the filtrate with stirring until the pH became 9, after which the mixture thus obtained was filtered to obtain a filtrate. The filtrate was evaporated to dryness to obtain 11.6 g of a brown powder. The powder is named "Sample 8".

The molecular weight distribution of Sample 8 was measured by aqueous system GPC to find that the proportion of compounds having a molecular weight of 500 or less was 5% by weight or less based on the total weight, and that a great peak appeared at a molecular weight of 4,300. The molecular weights were obtained by reduction from a calibration curve obtained by using, as standard substances, several sodium polystyrenesulfonates, sodium anthracenesulfonates and sodium benzenesulfonates different in molecular weight.

The solubility in water of Sample 8 was 30% by weight or more. Water was added to Sample 4 so as to prepare a 4% by weight aqueous solution, and the surface tension thereof was measured to find that it was 51.3 dyn/cm.

EXAMPLE 10

Condensation was conducted in the same manner as in Example 9, except that Sample 6 obtained in Example 7 was used, to obtain 10.1 g of a brown powder. The powder is named "Sample 9".

The molecular weight distribution of Sample 9 was measured in the same manner as in Example 9 to find that the proportion of compounds having a molecular weight of 500 or less was 3% by weight based on the total weight, and that a great peak appeared at a molecular weight of 4,800. The solubility in water of Sample 9 was 25% by weight or more. Water was added to Sample 9 so as to prepare a 4% by weight aqueous solution, and the surface tension thereof was measured to find that it was 50.8 dyn/cm.

EXAMPLE 11

In 50 g of distilled water was dissolved 2 g of each of Samples 5 to 9 obtained in Examples 6 to 10, to prepare five, in total, aqueous solutions. To each of the aqueous solutions was added 200 g of commercially available portland cement (manufactured by Chichibu Cement Co., Ltd.), and the mixtures thus obtained were individually kneaded by hand for 3 minutes, after which the flow values were measured by use of a flow corn with an inner volume of 98.9 cc according to JIS R5201. The results were as shown in Table 2.

TABLE 2

|  | Flow value (mm) |
|---|---|
| Sample 5 | 132 |
| Sample 6 | 130 |
| Sample 7 | 122 |

TABLE 2-continued

| | Flow value (mm) |
|---|---|
| Sample 8 | 163 |
| Sample 9 | 159 |

On the other hand, when the same treatment as described above was repeated, except that none of Samples 5 to 9 were added, the flow value was only 87 mm.

As can be seen from Examples 6 to 10, the compounds (2) and (3) of the present invention readily cause foaming and have an excellent surface active effect, and as can be seen from Example 11, when said compounds are used as dispersants for cement, they have a very great excellent effect on dispersing cement in water.

EXAMPLE 12

In a 3-liter, three-necked flask equipped with a reflux condenser and a stirrer were placed 1,270 g of toluene and 12 g of a boron trifluoride-phenol complex, and heated to 50° C., after which a mixed solution of 417 g of dicyclopentadiene and 320 g of toluene was added dropwise with stirring over a period of about 1 hour, and the resulting mixture was further subjected to reaction at said temperature for 2 hours. After completion of the reaction, the catalyst was decomposed with an aqueous sodium carbonate solution, and the reaction mixture was washed with water, after which the oil layer was distilled under reduced pressure to obtain 423 g of toluene adduct of dicyclopentadiene.

Subsequently, 200 g of the aforesaid toluene adduct of dicyclopentadiene, 97.8 g of sodium hydrogen-sulfite, 8.0 g of potassium nitrate, 1,360 ml of isopropyl alcohol and 200 ml of distilled water were placed in a 3-liter, stainless steel autoclave equipped with a stirrer and a thermometer, and air was supplied until the internal pressure in the autoclave became 1.0 kg/cm² (gauge pressure) at room temperature, after which the valve was locked up, and the mixture thus obtained was subjected to reaction at 110° C. for 5 hours while strongly stirring the mixture. Thereafter, the reaction mixture was allowed to stand at room temperature, after which the contents were taken out from the autoclave, and 50 ml of distilled water and 1,500 ml of petroleum ether were added to the contents. The resulting mixture was sufficiently stirred, and the separated petroleum ether layer and the precipitates were removed, after which the residue was concentrated to dryness to obtain 139 g of a light-yellow powder. The powder was subjected to extraction with petroleum ether by use of a Soxhlet's extractor for 1 hour to extract and remove unreacted matters, after which the residue was dried and then dissolved in 300 ml of glacial acetic acid, and an acetic acid-insoluble fraction consisting of inorganic salts was removed by filtration. The acetic acid-soluble fraction thus obtained was concentrated, to obtain 129 g of a whitish-yellow solid. This solid was purified by extraction with ethanol to obtain sodium salt of sulfonated toluene adduct of dicyclopentadiene.

Subsequently, 30 millimoles of the aforesaid sodium salt, 30 millimoles of formaldehyde, 30 millimoles of sulfuric acid and 270 millimoles of distilled water were charged into a 0.2-liter, three-necked flask equipped with a stirrer and a thermometer, and were subjected to condensation at 80° C. for 24 hours. After 100 g of distilled water was added to the resulting reaction mixture, calcium carbonate was added thereto with stirring until the pH became 7, and the resulting mixture was then filtered to obtain a filtrate. Sodium carbonate was added to the filtrate with stirring until the pH became 9, after which the mixture thus obtained was filtered to obtain a filtate. The filtrate was evaporated to dryness to obtain 11.2 g of a brown powder.

The infrared absorption spectrum of the brown powder is shown in FIG. 1. From the spectrum, it can be seen that a very strong absorption (1450 cm$^{-1}$) due to the scissoring vibration of condensed methylene group appears. The molecular weight of the product was measured by aqueous system GPC to find that the number average molecular weight was 4,900. Further, the composition of the brown powder was investigated by carrying out the quantitative analysis of the elements, to find that the composition was as follows: carbon atom 61.5%; hydrogen atom 6.8%; sulfur atom 10.1%.

From these results, the aforesaid brown powder was identified as a condensate of this invention represented by the structural formula (N):

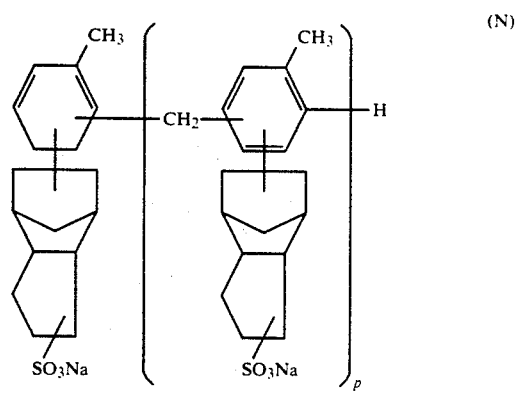

wherein p is an integer of 1 or more.

If p is taken as 14, then the composition of the structural formula was as follows: carbon atom 61.0%; hydrogen atom 7.1%; sulfur atom 9.9%. These values are in very good agreement with the found values described above.

EXAMPLE 13

The same procedure as in Example 12 was repeated, except that 1,060 g of xylene was substituted for the toluene and reacted with 350 g of dicyclopentadiene, to obtain 340 g of xylene adduct of dicyclopentadiene.

The same procedure as in Example 12 was repeated, except that 200 g of the xylene adduct was substituted for the toluene adduct, to obtain 124 g of sodium salt of sulfonated xylene adduct of dicyclopentadiene.

Subsequently, this sodium salt was subjected to condensation in the same manner as in Example 12 to obtain 10.3 g of a brown powder. The molecular weight thereof was measured by aqueous system GPC to find that the number average molecular weight was 5,400. Further, the composition of the brown powder was investigated by carrying out the quantitative analysis of the elements, to find that the composition was as follows: carbon atom 63.0%, hydrogen atom 7.5%; sulfur atom 9.4%.

From these results, the aforesaid brown powder was identified as a condensate of this invention having a structure obtained by replacing the toluene by xylene in the structural formula (N) shown in Example 12.

If p is taken as 15, then the composition of the structural formula of said condensate was as follows: carbon atom 62.1%; hydrogen atom 7.4%; sulfur atom 9.5%. These values are in very good agreement with the found values described above.

EXAMPLE 14

The same procedure as in Example 12 was repeated, except that 1,950 g of benzene was substituted for the toluene and reacted with 630 g of dicyclopentadiene, to obtain 203 g of a benzene adduct of dicyclopentadiene.

The same procedure as in Example 12 was repeated, except that 200 g of the benzene adduct was substituted for the toluene adduct to obtain 122 g of sodium salt of a sulfonated benzene adduct of dicyclopentadiene.

Subsequently, this sodium salt was subjected to condensation in the same manner as in Example 12 to obtain 10.1 g of a brown powder. The molecular weight was measured by aqueous system GPC to find that the number average molecular weight was 3,100. Further, the composition of the brown powder was investigated by carrying out the quantitative analysis of elements, to find that the composition was as follows: carbon atom 59.8%, hydrogen atom 6.8%; sulfur atom 10.6%.

From these results, the aforesaid brown powder was identified as a condensate of this invention having a structure obtained by replacing the toluene by benzene in the structural formula (N) shown in Example 12.

If p is taken as 9, then the composition of the structural formula of said condensate was as follows: carbon atom 59.9%; hydrogen atom 6.7%; sulfur atom 10.4%. These values are in very good agreement with the found values described above.

EXAMPLE 15

The same procedure as in Example 12 was repeated, except that the amount of the sulfuric acid was changed to 60 millimoles, to obtain a condensate of this invention. The molecular weight of the condensate was measured by aqueous system GPC to find that the number average molecular weight was 18,600 and that the molecular weight distribution ranges from 650 to 100,000.

EXAMPLE 16

In 30 g of distilled water was dissolved 1 g of the condensate obtained in Example 12, and brought into contact with 30 g of a cationic ion-exchange resin of a strong-acid type to obtain a condensate of this invention in which 98% of Na based on the calculated amount had been replaced by hydrogen.

EXAMPLE 17

An aqueous calcium hydroxide solution was added to the condensate in the acid form obtained in Example 16 with stirring until the pH became 7, to obtain a condensate in the calcium salt form of this invention in which the hydrogen atom was substituted by calcium atom.

EXAMPLE 18

In the same manner as in Example 12, 28.5 millimoles of the sodium salt of sulfonated toluene adduct of dicyclopentadiene obtained in Example 12, 1.5 millimoles of phenol, 30 millimoles of formaldehyde, 30 millimoles of sulfuric acid and 270 millimoles of distilled water were subjected to condensation, to obtain 9.6 g of a brown powder. The molecular weight of the brown powder was measured by aqueous system GPC to find that the number average molecular weight was 5,800. Further, the composition of the brown powder was investigated by carrying out the quantitative analysis of elements, to find that the values thus obtained agreed with the calculated values within a tolerance of 2%.

EXAMPLE 19

In the same manner as in Example 12, 7.5 millimoles of the sodium salt of sulfonated toluene adduct of dicyclopentadiene obtained in Example 12, 22.5 millimoles of toluene, 30 millimoles of formaldehyde, 30 millimoles of sulfuric acid and 270 millimoles of distilled water were subjected to condensation, to obtain 4.5 g of a yellowish-white powder. The molecular weight of the powder was measured by aqueous system GPC to find that the number average molecular weight was 4,200. The composition of the powder was investigated by carrying out the quantitative analysis of elements, to find that the values thus obtained agreed with the calculated values within a tolerance of 4%.

EXAMPLE 20

In the same manner as in Example 12, 20 millimoles of the sodium salt of sulfonated toluene adduct of dicyclopentadiene obtained in Example 12, 10 millimoles of sodium $\beta$-naphthalenesulfonate, 30 millimoles of formaldehyde, 30 millimoles of sulfuric acid and 270 millimoles of distilled water were subjected to condensation, to obtain 12.8 g of a brown powder. The molecular weight of the powder was measured by aqueous system GPC to find that the number average molecular amount was 4,300. Further, the composition of the powder was investigated by carrying out the quantitative analysis of elements, to find that the values thus obtained agreed with the calculated values within a tolerance of 4%.

EXAMPLE 21

There was prepared a 4% aqueous solution of each of the condensates of this invention obtained in Examples 12 to 20, and the surface tension thereof at 25° C. was measured. The results obtained are shown in Table 3.

TABLE 3

| Condensate | Surface tension (dyn/cm) |
|---|---|
| Example 12 | 43.8 |
| Example 13 | 42.2 |
| Example 14 | 46.1 |
| Example 15 | 45.2 |
| Example 16 | 47.2 |
| Example 17 | 44.3 |
| Example 18 | 41.5 |
| Example 19 | 36.5 |
| Example 20 | 59.8 |

As can be seen from the above results, the condensates of this invention readily caused foaming and had an excellent surface active effect.

To 200 g of commercially available cement portland cement (manufactured by Chichibu Cement Co., Ltd.) were added 2 g of the condensate of this invention obtained in Example 12 and 50 g of distilled water, and the resulting mixture was kneaded by hand for 3 minutes, after which the flow value (value measured by use of a flow corn with an inner volume of 98.9 cc according to JIS R5201) was measured to obtain a flow value of 150 mm. On the other hand, a mixture was kneaded by hand in the same manner as described above, except that the condensate of this invention was not added, after which the flow value was measured to obtain a flow value of only 87 mm. From these results, it can be seen that the condensate of this invention has a very great and excellent effect on dispersing cement in water.

EXAMPLE 22

A 30-liter, stainless steel autoclave equipped with a closed electromagnetic induction stirrer was used as a reactor. In the autoclave were placed 2,000 g of dicyclopentadiene having a purity of 95%, 1,200 g of sodium hydrogensulfite, 122 g of potassium nitrate, 8,000 ml of isopropyl alcohol and 2,000 ml of distilled water.

Subsequently, the autoclave was completely purged with nitrogen, and then sealed, after which the contents were subjected to reaction at 110° C. for 5 hours while strongly stirring the contents. After the reaction mixture was allowed to stand at room temperature, organic salts deposited from the reaction mixture were removed by suction filtration, and the filtrate was concentrated under reduced pressure to a volume of about 4 liters. To the concentrate were added 2.0 liters of distilled water and 1.5 liters of petroleum ether, and the resulting mixture was sufficiently stirred and then subjected to separation whereby unreacted dicyclopentadiene was extracted by the petroleum ether layer and removed.

The residue, i.e., the aqueous layer was concentrated to dryness under reduced pressure to obtain 2,300 g of a whitish-yellow solid. With the solid was mixed 4.0 liters of glacial acetic acid, and an acetic acid-insoluble fraction consisting of inorganic salts such as $NaHSO_3$, $Na_2SO_3$ and the like was separated by means of a centrifuge and removed.

An acetic acid-soluble fraction was concentrated to dryness under reduced pressure to obtain 1,480 g of a light-yellow solid. The light-yellow solid was subjected to extraction with ethanol having a purity of 99.5% by means of a Soxhlet's extractor for 1 hour to extract and remove the residual acetic acid, and then dried. The elementary analysis of the dried solid showed that C=50.4%; H=5.3%; S=14.0% (calculated value: C=50.8%; H=5.5%; S=13.6%). The solid was dissolved in water and freed from Na ion by using a cation-exchange resin, and the amount of sulfonic acid in the thus treated product was measured by titration to find that it was 102% of the calculated value.

As a result of the measurement of infrared absorption spectrum of the treated product by a KBr disc method, absorptions due to cyclopentene ring double bond appeared at 750 $cm^{-1}$ and 1,390 $cm^{-1}$, while an absorption due to norbornene ring double bond at 1570 $cm^{-1}$ observed in the case of dicyclopentadiene disappeared and in place thereof, absorptions due to sulfonic acid group were observed at 1,190 $cm^{-1}$ and 1,050 $cm^{-1}$; therefore it was confirmed that the nonbornene ring double bond had been sulfonated (see FIG. 2).

As a result of the analyses described above, the product was identified as a compound having the structural formula (O):

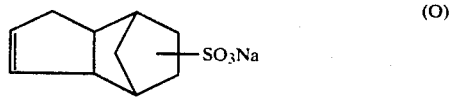

(O)

The surface tension at a temperature of 25° C. of a 4% by weight aqueous solution of the compound (O) was measured to find that it was 40 dyn/cm, indicating that the compound had a high surface activity.

The compound (O) was dissolved in distilled water, and freed from Na ion by means of a cation-exchange resin, after which the solution was concentrated to dryness to obtain a solid of the sulfonic acid type of the compound (O). Subsequently, 15 g of the sulfonic acid type of the compound (O) and 6.9 g of sulfuric acid having a purity of 97% were charged into a 300-ml, three-necked flask equipped with a reflux condenser and a stirrer, and subjected to polymerization at a reaction temperature of 120° C. for 25 hours with stirring.

After completion of the reaction, the sulfuric acid was removed by procedures of liming and sodation to obtain 15.5 g of the Na salt of a polymer.

The Na salt of a polymer was analized by gel permeation chromatography to obtain a graph having the main peak at a position corresponding to a number average molecular weight of 10,000.

The Na salt of a polymer was dissolved in distilled water and freed from Na ion by using a cation-exchange resin, and the amount of sulfonic acid in the thus treated product was measured by titration to find that the treated product had 0.96 sulfonic acid group per one molecule of the dicyclopentadiene.

The surface tension at 25° C. of a 4% by weight aqueous solution of the Na salt of a polymer was measured to find that it was 63 dyn/cm.

Subsequently, 2 g of the Na salt of a polymer was dissolved in 50 g of distilled water, and 200 g of Portland cement manufactured by Chichibu Cement Co., Ltd. was added. The resulting mixture was kneaded by hand for 3 minutes, and then subjected to a flow test by use of a flow corn having an inside diameter of 60 mmφ, a height of 35 mm and a capacity of 98.8 $cm^3$ according to the physical test method for cement of JIS R5201, whereby the flow value was determined as 190 mm. The specific gravity of green cement paste in this case was 2.23 $g/cm^3$. On the other hand, after 50 g of distilled water free from the Na salt of a polymer was kneaded with 200 g of Portland cement, the flow value was 87 mm and the specific gravity of green cement paste was 2.24 $g/cm^3$. From this, it can be seen that when the polymer of sulfonated dicyclopentadiene of this invention is used as a dispersant for cement, it has a very great and excellent effect on dispersing cement in water.

EXAMPLE 23. In 30-liter, stainless steel autoclave equipped with a stirrer and a thermometer were placed 3,000 g of dicyclopentadiene, 1,888 g of sodium hydrogensulfite, 91.7 g of potassium nitrate, 12 liters of isopropyl alcohol and 3,000 g of distilled water. Nitrogen was supplied thereto until the internal pressure in the autoclave became 1.0 kg/cm² (gauge pressure) at room temperature, after which the valve was locked up, and the mixture thus obtained were subjected to reaction at 110° C. for 5 hours while strongly stirring the mixture. Thereafter, the reaction mixture was allowed to stand at room temperature, and the major part of the isopropyl alcohol was removed by distillation, after which distilled water and petroleum ether were added, and the resulting mixture was sufficiently stirred. The separated petroleum ether layer and the precipitates were removed, and the aqueous layer thus obtained was concentrated and then evaporated to dryness. The concentrate was then dissolved in glacial acetic acid, and an acetic acid-insoluble fraction consisting of inorganic salts was separated by means of a centrifuge. The acetic acid-soluble fraction thus obtained was concentrated, to obtain 2,800 g of a white solid. The solid is named "Sulfonation Product A"

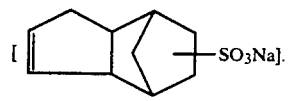

An aqueous solution of Sulfonation Product A was converted into the acid form, after which the aqueous solution was concentrated to dryness to obtain the acid form of the sulfonation product. This is named "Sulfonation Product B"

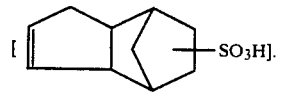

Subsequently, 15 g of Sulfonation Product B and 6.88 g of sulfuric acid were placed in a 300-ml, three-necked flask equipped with a reflux condenser and a stirrer, and subjected to polymerization at 120° C. for 26 hours. After completion of the reaction, the reaction mixture was subjected to liming and sodation. The amount of the thus obtained solid was 15.5 g, and the number average molecular weight of this polymer was 10,000. The polymer was named "Sample 10".

Sample 10 was converted into the acid form by means of an ion-exchange resin and titrated with potassium hydroxide to find that the polymer had 0.96 sulfonic acid group per one molecule of dicyclopentadiene.

Water was added to Sample 10 so as to prepare a 4% by weight aqueous solution, and the surface tension thereof at a temperature of 25° C. was determined as 63 dyn/cm.

The IR chart of Sample 10 is shown in FIG. 3, from which it can be seen that this polymer has sulfonic acid groups (1,190 cm⁻¹ and 1,050 cm⁻¹), and that the absorption due to double bond has become weak.

EXAMPLE 24

The same treatment as in Example 23 was repeated, except that Sulfonation Product A was used, to obtain a polymer having a number average molecular weight of 1,600. The polymer is named "Sample 11".

An aqueous solution of Sample 11 was converted into the acid form by means of an ion-exchange resin and titrated with potassium hydroxide solution to find that the polymer had 0.79 sulfonic acid group per one molecule of dicyclopentadiene.

The surface tension of a 4% by weight aqueous solution of Sample 11 was 69.2 dyn/cm.

EXAMPLE 25

The same procedure as in Example 23 was repeated, except that polymerization was conducted at a temperature of 170° C. for 28 hours by using 30 g of Sulfonation Product A, 125 g of sulfuric acid and 11.4 g of distilled water, to obtain a polymer having a number average molecular weight of 8,000. The polymer is named "Sample 12".

The degree of sulfonation was measured in the same manner as in Example 24 to find that Sample 12 had 0.59 sulfonic acid group per one molecule of dicyclopentadiene. The surface tension of a 4% by weight aqueous solution of the sample 12 was 65 dyn/cm.

EXAMPLE 26

In 50 g of distilled water was dissolved 2 g of each of Samples 10 to 12 to prepare four, in total, aqueous solutions. To each of the aqueous solutions was added 200 g of commercially available portland cement (manufactured by Chichibu Cement Co., Ltd.), and the mixture thus obtained was kneaded by hand for 3 minutes, after which the flow value was measured by use of a flow corn with an inner volume of 98.9 cc according to JIS R5201. The results obtained were as shown in Table 4.

TABLE 4

| | Flow value (mm) |
|---|---|
| Sample 10 | 205 |
| Sample 11 | 140 |
| Sample 12 | 170 |

On the other hand, the same treatment as in Example 26 was repeated, except that none of Samples 10 to 12 were added. The flow value in this cae was determined as only 87 mm.

As can be seen from Examples 23 to 25, the polymers of the sulfonation product of this invention have an excellent surface active effect, and as can be seen from Example 26, when they are used as dispersants for cement, they have a very great and excellent effect on dispersing cement in water.

EXAMPLE 27

In a 300-ml, three-necked flask equipped with a reflux condenser and a stirrer were placed 13 g of Sulfonation Product A, 2 g of dicyclopentadiene and 6.88 g of sulfuric acid, and the resulting mixture was subjected to copolymerization at a temperature of 120° C. for 20 hours. After the reaction, the reaction mixture was subjected to liming and sodation. The amount of the solid thus obtained was 15.0 g, and the surface tension of a 4% by weight aqueous solution of the obtained copolymer was 40 dyn/cm, namely, the copolymer had an excellent surface active effect.

EXAMPLE 28

A 30-liter, stainless steel autoclave equipped with a closed electromagnetic induction stirrer was used as a reactor. In the autoclave were placed 2,000 g of hydroxydicyclopentadiene, 2,000 g of sodium hydrogensulfite, 200 g of potassium nitrate, 8,000 ml of isopropyl alcohol and 2,000 ml of distilled water.

Subsequently, the autoclave was completely purged with nitrogen, and then sealed, after which the resulting mixture was subjected to reaction at 110° C. for 5 hours while strongly stirring the mixture. After the reaction mixture was allowed to stand at room temperature, organic salts deposited from the reaction mixture were removed by suction-filtration, and the filtrate was concentrated under reduced pressure to a volume of about 4 liters.

To the concentrate were added 2.0 liters of distilled water and 1.5 liters of petroleum ether, and the resulting mixture was sufficiently stirred and then subjected to separation, whereby unreacted hydroxydicyclopentadiene was extracted into the petroleum ether layer and removed.

The residue, i.e., the aqueous layer, was concentrated to dryness under reduced pressure to obtain 2,600 g of a whitish-yellow solid. With the solid was mixed 4.0 liters of glacial acetic acid, and an acetic acid-insoluble fraction consisting of organic salts such as $NaHSO_3$, $Na_2SO_3$ and the like was separated by means of a centrifuge and removed.

The acetic acid-soluble fraction thus obtained was concentrated to dryness under reduced pressure to obtain 2,300 g of a light-yellow solid. The light-yellow solid was subjected to extraction with ethanol having a purity of 99.5% by means of a Soxhlet's extractor for 1 hour to extract and remove the residual acetic acid, and then dried. The elementary analysis of the dried solid showed that C=47.9%; H=6.2%; S=12.9% (values calculated from the molecular formula: C=47.2%; H=5.9%; S=12.6%). The solid was dissolved in water and freed from Na ion by using a cation-exchange resin, after which the amount of sulfonic acid in the thus treated product was determined by titration as 93% of the calculated value.

As a result of the measurmenet of infrared absorption spectrum of the treated product by a KBr disc method, an absorption due to hydroxyl group appeared at 3,440 $cm^{-1}$, while absorptions due to cyclopentene ring double bond at 750 $cm^{-1}$ and 1,390 $cm^{-1}$ observed in the case of dicyclopentadiene diminished and in place of thereof, strong absorptions due to sulfone group were observed at 1,190 $cm^{-1}$ and 1,050 $cm^{-1}$. Therefore, it was confirmed that the cyclopentene ring double bond had been sulfonated (see FIG. 4).

As a result of the analysis described above, the product was identified as a compound having the structural formula (P):

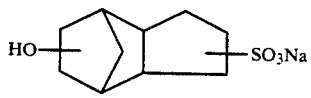

(P)

The surface tension at a temperature of 25° C. of a 4% by weight aqueous solution of the compound was determined as 40 dyn/cm, indicating that the compound had a high surface active effect.

The aforesaid compound (P) was dissolved in distilled water, and freed from Na ion by means of a cation-exchange resin, after which the solution was concentrated to dryness, to obtain a solid of sulfonic acid of the aforesaid compound (P).

Subsequently, 30 g of the sodium sulfonate of the aforesaid compound (P) and 57 g of sulfuric acid having a purity of 97% were charged into a 300-ml three-necked flask equipped with a reflux condenser and a stirrer, and subjected to polymerization at a reaction temperature of 130° C. for 20 hours with stirring.

After completion of the reaction, the sulfuric acid was removed by procedures of liming and sodation to obtain 31 g of Na salt of a polymer.

The Na salt of a polymer was analyzed by gel permeation chromatography to obtain a chromatograph having the main peak at a position corresponding to a molecular weight of 4,000.

The Na salt of a polymer was dissolved in distilled water and freed from Na ion by using a cation-exchange resin, and the amount of sulfonic acid in the thus treated product was measured by titration to find that the treated product had sulfonic acid groups in a proportion of 88 mole% based on the hydroxypentadiene.

The surface tension at 25° C. of a 4% by weight aqueous solution of the Na salt of a polymer was determined as 68 dyn/cm.

Subsequently, 2 g of Na salt of a polymer was dissolved in 50 g of distilled water, and 200 g of portland cement manufactured by Chichibu Cement Co., Ltd. was added, after which the resulting mixture was kneaded for 3 minutes. Thereafter, a flow corn having an inside diameter of 60 mmφ, a height of 35 mm and a capacity of 98.8 $cm^3$ was produced, and the kneaded mixture was subjected to a flow test by use of the flow corn according to the physical test method for cement of JIS R5201, whereby the flow value was determined as 160 mm.

The specific gravity of green cement paste in this case was 2.17 $g/cm^3$.

On the other hand, when the Na salt of a polymer was not added, the flow value was 87 mm and the specific gravity of green cement paste was 2.24 $g/cm^3$.

From this fact, it can be seen that when the polymer of sulfonated hydroxydicyclopentadiene of this invention is used as a dispersant for cement, it has a very great and excellent effect on dispersing cement in water.

EXAMPLE 29

In a 3-liter, three-necked flask equipped with a reflux condenser and a stirrer were placed 1,270 g of toluene and 12 g of a boron trifluoride-phenol complex, and the temperature was raised to 50° C., after which a mixed solution of 417 g of dicyclopentadiene and 320 g of toluene was added dropwise with stirring over a period of about 1 hour, and the resulting mixture was subjected to reaction at said temperature for an additional 2 hours. After completion of the reaction, the catalyst was decomposed with an aqueous sodium carbonate solution, and the reaction mixture was washed with water, after which the oil layer was distilled under reduced pressure to obtain 423 g of toluene adduct of dicyclopentadiene.

Subsequently, 200 g of the aforesaid toluene adduct of dicyclopentadiene, 97.8 g of sodium hydrogensulfite, 8.0 g of potassium nitrate, 1,360 ml of isopropyl alcohol and 200 ml of distilled water were placed in a 3-liter, stainless steel autoclave equipped with a stirrer and a thermometer, and air was supplied until the internal pressure in the autoclave became 1.0 kg/cm² (gauge pressure) at room temperature. Then the valve was locked up, and the mixture thus prepared was subjected to reaction at a temperature of 110° C. for 5 hours with strong stirring. Thereafter, the reaction mixture was allowed to stand at room temperature, after which the contents were taken out of the autoclave. To the contents were added 50 ml of distilled water and 1,500 ml of petroleum ether, and the resulting mixture was sufficiently stirred. The separated petroleum ether layer and the precipitates were removed, and the residue obtained was concentrated to dryness, to obtain 139 g of a light yellow powder. The powder was subjected to extraction with petroleum ether by use of a Soxhlet's extractor for 1 hour to extract and remove the unreacted materials, after which the residue was dried and then dissolved in 300 ml of glacial acetic acid, and an acetic acid-insoluble fraction consisting of inorganic salts was removed by filtration. The thus obtained acetic acid-soluble fraction was concentrated to obtain 129 g of whitish yellow solid. This solid was purified by extraction with ethanol to obtain the sodium salt of sulfonated toluene adduct of cyclopentadiene. The sodium salt is named "Sample 13".

Subsequently, 60 millimoles of Sample 13 and 80 millimoles of sulfuric acid were charged into a 0.2-liter, three-necked flask equipped with a stirrer and a thermometer, and subjected to reaction at 100° C. for 3 hours. Thereafter, 10 cc of n-heptane was added, and the azeotropic removal of n-heptane and $H_2O$ was carried out at 110° C. for 2 hours and then at 80° C. under reduced pressure. The product thus obtained is named "Sample 14".

Subsequently, 6.3 g of $H_2O$ was poured into Sample 14 (60 millimoles), and 5.35 g (66 millimoles) of a 37% aqueous formaldehyde solutoin was added dropwise at 80° C. over a period of 3 horus, after which the temperature was raised to 100° C., and reaction was effected for 20 hours to obtain a viscous condensate. The condensate was dissolved in 100 g of water, and the pH of the resulting solution was adjusted to 7 by the addition of 11 g of $CaCO_3$, after which the thus formed white precipitates were separated by filtration. To the filtrate was further added 3.2 g of $Na_2CO_3$, and the resulting white precipitates were removed by filtration. The filtrate is named "Sample 15".

For the thus obtained Samples 14 and 15, the proportions of sulfonic acid per mole of the toluene adduct of dicyclopentadiene were measured by a conventional method to find that they were 1.92 moles and 1.75 moles, respectively, so that it became apparent that the degree of sulfonation with respect to the skeleton was about 2. Elementary analysis was carried out for Sample 14 to obtain the following results: carbon 51.2%, hydrogen 5.3%, sulfur 15.4%, oxygen 23.2%, which were in good agreement with the theoretical values for the disulfonation product, C=50.0%, H=5.1%, S=15.7%, O=23.5%. The number average molecular weight of Sample 15 was 6,300 as measured by GPC. Subsequently, the result of infrared analysis of Sample 15 is shown in FIG. 5, from which it can be seen that absorptions due to sulfonic acid group at 1,050 cm$^{-1}$ and 1,190 cm$^{-1}$ are very strong and that an absorption due to methylene group at 1,450 cm$^{-1}$ is also strong. This indicates that the condensation proceeded and that Sample 15 is a sulfonation product.

The surface tension of a 4% aqueous solutoin of Sample 15 was as very high as 63 dyn/cm and the solution was only slightly foamed.

EXAMPLE 30

By the same procedure as in Example 29, 89 g of a sulfonation product of the xylene adduct of dicyclopentadiene was obtained.

The sulfonation product was subjected to disulfonation and then condensation in the same manner as in Example 29. The acid values of the disulfonation product and the condensate were 1.76 moles and 1.58 moles, respectively, per mole of the skeleton. The surface tension of a 4% aqueous solutoin of the condensate was as high as 61 dyn/cm. The number average molecular weight of the condensate was 4,500.

EXAMPLE 31

The same procedure as in Example 29 was repeated, except that the amount of Sample 14 was changed from 60 millimoles to 45 millimoles and that Sample 14 was condensed with 15 millimoles of phenol. The number average molecular weight of the resulting condensate was 7,800, and the surface tension of a 4% aqueous solution of the condensate was as high as 58 dyn/cm.

EXAMPLE 32

The same procedure as in Example 29 was repeated, except that the amount of Sample 14 was changed from 60 millimoles to 30 millimoles and that 30 millimoles of Sample 13 was substituted for the balance and condensed with Sample 14. The number average molecular weight of the resulting condensate was 6,800, and the surface tension of a 4% aqueous solution of the condensate was as high as 58 dyn/cm.

EXAMPLE 33

The same procedure as in Example 29 was repeated, except that the amount of Sample 14 was changed from 60 millimoles to 30 millimoles and that 30 millimoles of β-naphthalenesulfonic acid was substituted for the balance and condensed with Sample 14. The number average molecular weight of the resulting condensate was 8,900, and the surface tension of a 4% aqueous solution of the condensate was as very high as 67 dyn/cm.

EXAMPLE 34

To 200 g of commercially available Portland cement (manufactured by Chichibu Cement Co., Ltd.) were added 2 g of each of the condensates obtained in Examples 29 to 33 and 50 g of distilled water, and the resulting mixture was kneaded by hand for 3 minutes. Thereafter, the flow values were measured by use of a flow corn with an inner volume of 98.9 cc according to JIS R5201. The flow values and the specific gravities of green cement pastes are shown in Table 5. It can be seen therefrom that in this case the cement showed excellent dispersability and no air-entraining property.

COMPARATIVE EXAMPLE

The same flow test as in Example 34 was repeated, except that the condensates of this invention were not added. The results are shown in Table 5.

TABLE 5

| Additive | Flow value (mm) | Specific gravity (g/cc) |
|---|---|---|
| Condensate of Example 29 | 187 | 2.21 |

TABLE 5-continued

| Additive | Flow value (mm) | Specific gravity (g/cc) |
| --- | --- | --- |
| Condensate of Example 30 | 171 | 2.18 |
| Condensate of Example 31 | 157 | 2.15 |
| Condensate of Example 32 | 180 | 2.19 |
| Condensate of Example 33 | 184 | 2.21 |
| None (Comparative Example) | 87 | 2.20 |

EXAMPLE 35

In a 300-ml, three-necked flask equipped with a reflux condenser and a stirrer were placed 15 g of sulfonated hydroxydicyclopentadiene (M in the formula (G)=H) and 6.88 g of sulfuric acid, and the resulting mixture was subjected to polymerization at 120° C. for 23 hours. After completion of the reaction, the reaction mixture was subjected to liming and sodation. The amount of the thus obtained solid was 15.5 g, and the number average molecular weight of this polymer was 10,000. The solid is named "Sample 15".

Sample 15 was converted into the acid form by means of an ion-exchange resin and titrated with potassium hydroxide to find that it had 0.97 sulfonic acid groups per one molecule of dicyclopentadiene.

Water was added to Sample 15 so as to prepare a 4% by weight aqueous solution, and the surface tension at a temperature of 25° C. was determined as 65 dyn/cm.

The IR chart of the polymer is shown in FIG. 6, from which it can be seen that the polymer has sulfonic acid groups and that the absorption due to —OH group at 3,450 cm$^{-1}$ becomes weak.

EXAMPLE 36

In a 300-ml, three-necked flask equipped with a reflux condenser and a stirrer were placed 8 g of sulfonated hydroxydicyclopentadiene (M in the formula (G)=H), 7 g of sulfonated dicyclopentadiene having the structural formula:

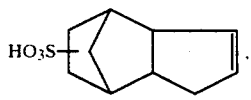

and 6.88 g of sulfuric acid, and subjected to polymerization at 120° C. for 20 hours. After the reaction, the reaction mixture was subjected to liming and sodation. The amount of the solid thus obtained (named "Sample 16") was 15.5 g, and the surface tension of a 4% by weight aqueous solution of the copolymer thus obtained was 64 dyn/cm. The number average molecular weight of the polymer was 10,000.

EXAMPLE 37

In a 300-ml, three-necked flask equipped with a reflux condenser and a stirrer were placed 13 g of sulfonated hydroxydicyclopentadiene (M in the general formula (G)=H), 2 g of acrylic acid and 6.88 g of sulfuric acid, and the resulting mixture was subjected to polymerization at a temperature of 120° C. for 20 hours. After the reaction, the reaction mixture was subjected to liming and sodation. The amount of the solid thus obtained (names "Sample 17") was 15.4 g, and the surface tension of a 4% by weight aqueous solution of the copolymer thus obtained was 50 dyn/cm. The number average molecular weight of the copolymer was 10,000. From IR, an absorption due to the carbonyl group of acrylic acid was observed, and the reaction was proved to be copolymerization.

EXAMPLE 38

In the same reactor as in Examples 35 to 37 were placed 13 g of sulfonated hydroxydicyclopentadiene (M in the general formula (G)=H), 2 g of β-naphthalenesulfonic acid and 6.88 g of sulfuric acid, and the resulting mixtue was subjected to copolymerization at a temperature of 120° C. for 20 hours. After the reaction, the reaction mixture was subjected to liming and sodation. The amount of the solid thus obtained (named "Sample 18") was 15.5 g, and the surface tension of a 4% by weight aqueous solution of the obtained copolymer was 64 dyn/cm. The number average molecular weight of the copolymer was 10,000. From IR, an absorption due to naphthalene ring was observed, and the reaction was proved to be copolymerization.

EXAMPLE 39

In 50 g of distilled water was dissolved 2 g of each of Samples 15 to 18 to prepare four, in total, aqueous solutions. To each of the aqueous solutions was added 200 g of commercially available Portland cement (manufactured by Chichibu Cement Co., Ltd.), and the resulting mixture was kneaded by hand for 3 minutes, after which the flow value was measured by using a flow corn with an inner volume of 98.9 cc (JIS R5201). The results obtained were as shown in Table 6.

TABLE 6

|  | Flow value (mm) |
| --- | --- |
| Sample 15 | 200 |
| Sample 16 | 205 |
| Sample 17 | 185 |
| Sample 18 | 195 |

On the other hand, when the same treatment as described above was repeated, except that none of Samples 15 to 18 were added, the flow value was only 87 mm.

As can be seen from Examples 35 to 38, the polymers of the sulfonation products of this invention have an excellent surface active effect, and as can be seen from Example 39, when the polymers of the sulfonation products of this invention are used as dispersants for cement, they have a very excellent effect on dispersing cement in water.

EXAMPLE 40

(1) Synthesis of dispersant

With 1,570 g of toluene was reacted 417 g of dicyclopentadiene in the presence of 12 g of a boron trifluoride-phenol complex at 50° C. for 3 hours. Thereafter, the reaction solution was washed with an alkali, and thereafter distilled, to obtain 423 g of a toluene adduct of dicyclopentadiene.

To 200 g of the toluene adduct of dicyclopentadiene were added 97.8 g of sodium hydrogensulfite, 8.0 g of potassium nitrate, 1,360 ml of isopropyl alcohol and 200 ml of water, and the resulting mixture was subjected to reaction in air at a temperature of 110° C. for 5 hours. Subsequently, unreacted materials were extracted with petroleum ether, after which the residue was evaporated to dryness and then dissolved in acetic acid to remove unreacted inorganic materials, and the acetic acid-soluble fraction thus obtained was concentrated to obtain 129 g of a whitish-yellow powder. The powder was analyzed to identify it as sodium sulfonate of toluene adduct of dicyclopentadiene represented by the following structural formula (which is named "Monomer A"):

Subsequently, 0.1 mole of Monomer A, 0.1 mole of formaldehyde, 0.1 mole of sulfuric acid and 0.9 mole of water were charged into a reactor, and subjected to condensation reaction at a temperature of 80° C. for 24 hours. After 500 g of water was added to the reaction mixture, calcium carbonate was added with stirring until the pH became 7, after which the resulting mixture was filtered to obtain a filtrate, and calcium carbonate was added to the filtrate with stirring until the pH became 9. Thereafter, the white precipitate formed was removed by filtration, and the thus obtained filtrate was evaporated to dryness to obtain 33.6 g of a condensate of Monomer A through formaldehyde in the form of a brown powder. The condensate is named "Dispersant B".

(2) Synthesis of polymer emulsion

In a 1-liter autoclave were placed 400 g of water, 3 g of sodium dodecylbenzenesulfonate and 0.2 g of potassium persulfate, and polymerization was effected by continuously adding thereto dropwise 200 g of ethyl acrylate at a temperature of 80° C. with stirring over a period of 2 hours, whereby a polymer emulsion was synthesized. The degree of polymerization reached 100% in 3 hours after the initiation of the polymerization. The polymer emulsion is named "Polymer Emulsion C".

To 500 g of a normal portland cement (manufactured by Chichibu Cement Co., Ltd.) were added 3.5 g of Dispersant B and 0.35 g (as solids) of Polymer Emulsion C which had been synthesized in the manner described above, and 125 g of water was further added, after which the resulting mixture was stirred at a revolution rate of 120 r.p.m. to prepare a cement paste. This product is named "Sample 19".

EXAMPLE 41

A cement paste was prepared in the same manner as in Example 1, except for the use of 3.5 g of Dispersant B and 0.15 g (as solids) of the polymer emulsion which had been synthesized in Example 40. The cement paste is named "Sample 20".

EXAMPLE 42

A cement paste was prepared in the same manner as in Example 40, except for the use of 3.5 g of Dispersant B and 1.0 g (as solids) of Polymerization Emulsion C which had been synthesized in Example 40. The cement paste is named "Sample 21".

COMPARATIVE EXAMPLE 2

A cement paste for comparison was prepared in the same manner as in Example 40, except that the Polymer Emulsion C was not used and that 3.5 g of Dispersant B was used. It is named "Comparative Sample 1".

COMPARATIVE EXAMPLE 3

A cement paste for comparison was prepared in the same manner as in Example 40, except that Dispersant B was not used and that 0.15 g (as solids) of Polymer Emulsion C was used. The cement paste is named "Comparative Sample 2".

COMPARATIVE EXAMPLE 4

A cement paste for comparison was prepared in the same manner as in Example 40, except that neither Dispersant B nor Polymer Emulsion C were used. The cement paste is named "comparative Sample 3".

The flow values and the specific gravities of Samples 19 to 21 and Comparative Samples 1 to 3 were measured. The results obtained were as shown in Table 7. The flow values were measured by use of a flow corn with an inner volume of 89.9 cc according to JIS R5201, and the specific gravities of the cement paste were also measured according to JIS R5201.

TABLE 7

|  | Ratio of dispersant B to cement (% by weight) | Ratio of polymer Emulsion C (as solids) to cement (% by weight) | Stirring time (min) | Flow value (mm) | Specific gravity of cement paste (g/cc) |
|---|---|---|---|---|---|
| Sample 19 | 0.7 | 0.07 | 3 | 155 | 2.25 |
|  |  |  | 30 | 150 | 2.26 |
|  |  |  | 60 | 130 | 2.27 |
| Sample 20 | 0.7 | 0.03 | 3 | 150 | 2.23 |
|  |  |  | 30 | 143 | 2.25 |
| Sample 21 | 0.7 | 0.03 | 3 | 155 | 2.25 |
|  |  |  | 30 | 153 | 2.27 |
| Comparative Sample 1 | 0.7 | 0 | 3 | 155 | 1.90 |
|  |  |  | 30 | 153 | 1.87 |
| Comparative Sample 2 | 0 | 0.20 | 3 | 85 | 2.25 |
| Comparative Sample 3 | 0 | 0 | 3 | 87 | 2.26 |

EXAMPLE 43

A polymer emulsion was synthesized in the same manner as in the synthesis of a polymer emulsion in Example 40, except that butyl acrylate was substituted for the ethyl acrylate. A cement paste was prepared in the same manner as in Example 40, except that the thus obtained polymer emulsion was substituted for the Polymer Emulsion C. This cement paste is named "Sample 22".

EXAMPLE 44

A polymer emulsion was synthesized in the same manner as in the synthesis of a polymer emulson in Example 40, except that styrene was substituted for the ethyl acrylate. A cement paste was prepared in the same manner as in Example 40, except that the thus obtained polymer emulsion was substituted for the Polymer Emulsion C. This cement paste is named "Sample 23".

EXAMPLE 45

A polymer emulsion was synthesized in the same manner as in the synthesis of a polymer emulsion in Example 40, except that the ethyl acrylate was replaced by a mixture of 20% by weight of ethyl acrylate and 80% by weight of styrene. A cement paste was prepared in the same manner as in Example 40, except that the thus obtained polymer emulsion was substituted for the Polymer Emulsion C. This cement paste is named "Sample 24".

EXAMPLE 46

A polymer emulsion was synthesized in the same manner as in the synthesis of a polymer emulsion in Example 40, except that methyl methacrylate was substituted for the ethyl acrylate. A cement paste was prepared in the same manner as in Example 40, except that the thus obtained polymer emulsion was substituted for the Polymer Emulsion C. This cement paste is named "Sample 25".

EXAMPLE 47

A polymer emulsion was synthesized in the same manner as in the synthesis of a polymer emulsion in Example 40, except that vinyl acetate was substituted for the ethyl acrylate. A cement paste was prepared in the same manner as in Example 40, except that the thus obtained polymer emulsion was substituted for the Polymer Emulsion C. The cement paste is named "Sample 26".

EXAMPLE 48

A polymer emulsion was synthesized in the same manner as in the synthesis of a polymer emulsion in Example 40, except that the ethyl acrylate was replaced by a mixture of 30% by weight of butadiene, 68% by weight of styrene and 2% by weight of itaconic acid. A cement paste was prepared in the same manner as in Example 40, except that the thus obtained polymer emulsion was substituted for the Polymer Emulsion C. This cement paste is named "Sample 27".

The flow values and the specific gravities of Samples 22 to 27 were measured in the same manner as in Table 7. The results obtained were as shown in Table 8.

TABLE 8

|  | Stirring time (min) | Flow value (mm) | Specific gravity of cement paste (g/cc) |
|---|---|---|---|
| Sample 22 | 3 | 160 | 2.19 |
|  | 30 | 157 | 2.26 |
| Sample 23 | 3 | 133 | 2.05 |
|  | 30 | 118 | 2.07 |
| Sample 24 | 3 | 146 | 2.15 |
|  | 30 | 138 | 2.18 |
| Sample 25 | 3 | 136 | 2.01 |
|  | 30 | 120 | 2.06 |
| Sample 26 | 3 | 135 | 2.10 |
|  | 30 | 123 | 2.11 |
| Sample 27 | 3 | 130 | 2.07 |
|  | 30 | 115 | 2.08 |

EXAMPLE 49

A cement paste was prepared in the same manner as in Example 40, except that the Polymer Emusion C was replaced by a commercially available latex "JSR #0598" (manufactured by Japan Synthetic Rubber Co., Ltd.). The cement paste is named "Sample 28".

EXAMPLE 50

A cement paste was prepared in the same manner as in Example 40, except that the Polymer Emulsion C was replaced by a commercially available latex "JSR #696" (manufactured by Japan Synthetic Rubber Co., Ltd.). The cement paste is named "Sample 29".

EXAMPLE 51

A cement paste was prepared in the same manner as in Example 40, except that the Polymer Emulsion C was replaced by a commercially available latex "JSR Tomack Super" (manufactured by Japan Synthetic Rubber Co., Ltd.). The cement paste is named "Sample 30".

EXAMPLE 52

A cement paste was prepared in the same manner as in Example 40, except that the Polymer Emulsion C was replaced by a commercially available latex "JSR #2108" (manufactured by Japan Synthetic Rubber Co., Ltd.). The cement paste is named "Sample 31".

The flow values and the specific gravities of Samples 28 to 31 were measured in the same manner as in Table 7. The results obtained were as shown in Table 9.

TABLE 9

|  | Stirring time (min) | Flow value (mm) | Specific gravity of cement paste (g/cc) |
|---|---|---|---|
| Sample 28 | 3 | 130 | 2.02 |
|  | 30 | 122 | 2.01 |
| Sample 29 | 3 | 128 | 2.02 |
|  | 30 | 120 | 2.00 |
| Sample 30 | 3 | 138 | 2.03 |
|  | 30 | 130 | 2.05 |
| Sample 31 | 3 | 130 | 1.98 |
|  | 30 | 119 | 2.01 |

COMPARATIVE EXAMPLE 5

A cement paste for comparison was prepared in the same manner as in Example 40, except that the Polymer Emulsion C was replaced by sodium polyacrylate which is a water-soluble polymer. The cement paste is named "Comparative Sample 4".

COMPARATIVE EXAMPLE 6

A cement paste for comparison was prepared in the same manner as in Example 40, except that the Polymer Emulsion C was replaced by polyvinyl alcohol which is a water-soluble polymer. The cement paste is named "Comparative Sample 5".

COMPARATIVE EXAMPLE 7

A cement paste for comparison was prepared in the same manner as in Example 40, except that the Polymer Emulsion C was replaced by a sodium-neutralization product obtained by neutralizing a water-soluble polymer of 50% by weight of methyl methacrylate and 50% by weight of methacrylic acid with sodium hydroxide. The cement paste is named "Comparative Sample 6".

The flow values and the specific gravities of Comparative Samples 5 to 7 were measured in the same manner as in Table 7. The results obtained were as shown in Table 10.

TABLE 10

| | Stirring time (min) | Flow value (mm) | Specific gravity of cement paste (g/cc) |
|---|---|---|---|
| Comparative Sample 4 | 3 | 90 | 1.77 |
| Comparative Sample 5 | 3 | 119 | 1.91 |
| | 15 | 97 | 1.88 |
| Comparative Sample 6 | 3 | 116 | 1.89 |
| | 15 | 98 | 1.86 |

EXAMPLE 53

A cement paste was prepared in the same manner as in Example 40, except that the Dispersant B was replaced by a commercially available dispersant "Mighty 150" (manufactured by Kao Soap Co., Ltd.) consisting of a high-condensate of sodium naphthalenesulfonate. The cement paste is named "Sample 32".

COMPARATIVE EXAMPLE 8

A cement paste was prepared in the same manner as in Example 53, except that the Polymer Emulsion C was not used. The cement paste is named "Comparative Sample 7".

EXAMPLE 54

A cement paste was prepared in the same manner as in Example 40, except that the Dispersant B was replaced by a commercially available dispersant "NP20" (manufactured by Nisso Master Builders Co., Ltd.) consisting of a condensate of sodium melaminesulfonate. The cement paste is named "Sample 33".

COMPARATIVE EXAMPLE 9

A cement paste for comparison was prepared in the same manner as in Example 54, except that the Polymer Emulsion C was not used. The cement paste is named "Comparative Sample 8".

EXAMPLE 55

A cement paste was prepared in the same manner as in Example 40, except that the Dispersant B was replaced by a commercially available dispersant "Sunflo PS" (manufactured by Sanyo-Kokusaku Pulp Co., Ltd.) consisting of a co-condensate of sodium naphthalenesulfonate with sodium lignin sulfonate. The cement paste is named "Sample 34".

COMPARATIVE EXAMPLE 10

A cement paste for comparison was prepared in the same manner as in Example 55, except that the Polymer Emulsion C was not used. The cement paste is named "Comparative Sample 9".

EXAMPLE 56

A cement paste was prepared in the same manner as in Example 40, except that the Dispersant B was replaced by a commercially available dispersant "Plastocrete NC" (Nihon Sika Co., Ltd.) consisting of sodium lignin sulfonate. The cement paste is named "Sample 35".

COMPARATIVE EXAMPLE 11

A cement paste for comparison was prepared in the same manner as in Example 56, except that the Polymer Emulsion C was not used. The cement paste is named "Comparative Sample 10".

The flow values and the specific gravities of Samples 32 to 35 and Comparative Samples 7 to 10 were measured in the same manner as in Table 7. The results obtained were as shown in Table 11.

TABLE 11

| | Stirring time (min) | Flow value (mm) | Specific gravity of cement paste (g/cc) |
|---|---|---|---|
| Sample 32 | 3 | 158 | 2.26 |
| | 30 | 140 | 2.26 |
| | 60 | 120 | 2.26 |
| Comparative Sample 7 | 3 | 155 | 2.27 |
| | 30 | 110 | 2.27 |
| Sample 33 | 3 | 145 | 2.29 |
| | 30 | 135 | 2.28 |
| | 60 | 126 | 2.29 |
| Comparative Sample 8 | 3 | 135 | 2.26 |
| | 30 | 120 | 2.29 |
| Sample 34 | 3 | 138 | 2.23 |
| | 30 | 127 | 2.24 |
| Comparative Sample 9 | 3 | 120 | 1.90 |
| | 30 | 90 | 1.90 |
| Sample 35 | 3 | 106 | 2.20 |
| | 30 | 93 | 2.20 |
| Comparative Sample 10 | 3 | 100 | 2.06 |
| | 30 | 87 | 2.06 |

EXAMPLE 57

In a 1-liter autoclave were placed 400 g of water, 0.4 g of sodium dodecylbenzenesulfonate and 0.2 g of potassium persulfate, and polymerization was effected by continuously dropping thereinto 200 g of ethyl acrylate at a temperature of 80° C. with stirring over a period 2 hours, to obtain a polymer emulsion. The polymerization conversion reached 100% in 3 hours after the initiation of the polymerization. The polymer emulsion is named "Polymer Emulsion D".

To 500 g of a normal portland cement (manufactured by Chichibu Cement Co., Ltd.) were added 3.5 g of Dispersant B and 0.35 g (as solids) of Polymer Emulsion D, and 125 g of water was further added, after which the resulting mixture was stirred at a revolution rate of 120 r.p.m. to prepare a cement paste. This cement paste is named "Sample 36".

EXAMPLE 58

A polymer emulsion was synthesized in the same manner as in the synthesis of a polymer emulsion in Example 57, except that the amount of sodium dodecylbenzenesulfonate was changed to 1 g. A cement paste was prepared in the same manner as in Example 57, except that the thus obtained polymer emulsion was substituted for the Polymer Emulsion D. This cement paste is named "Sample 37".

EXAMPLE 59

A polymer emulsion was synthesized in the same manner as in the synthesis of a polymer emulsion in Example 57, except that the amount of sodium dodecylbenzenesulfonate was changed to 2 g. A cement paste was prepared in the same manner as in Example 57, except that the thus obtained polymer emulsion was substituted for the Polymer Emulsion D. This cement paste was named "Sample 38".

COMPARATIVE EXAMPLE 12

A polymer emulsion was synthesized in the same manner as in the synthesis of a polymer emulsion in Example 57, except that the amount of sodium dodecylbenzenesulfonate was changed to 3 g. A cement paste for comparison was prepared in the same manner as in Example 57, except that the thus obtained polymer emulsion was substituted for the Polymer Emulsion D. This cement paste is named "Comparative Sample 11".

The flow values of Samples 36 to 38 and Comparative Sample 11 were measured in the same manner as in Table 7. The results obtained were as shown in Table 12.

TABLE 12

| | Amount of surfactant per 100 parts by weight of polymerizable monomer (part by weight) | Stirring time (min) | Flow value (mm) |
|---|---|---|---|
| Sample 36 | 0.2 | 3 | 163 |
| | | 30 | 160 |
| | | 60 | 148 |
| Sample 37 | 0.5 | 30 | 158 |
| | | 60 | 144 |
| Sample 38 | 1.0 | 30 | 155 |
| | | 60 | 138 |
| Comparative Sample 11 | 1.5 | 3 | 154 |
| | | 30 | 148 |
| | | 60 | 127 |

EXAMPLE 60

In a 1-liter autoclave were placed 400 g of water, 1.0 g of sodium dodecylbenzenesulfonate and 0.2 g of potassium persulfate, and a mixed solution of 140 g of styrene, 58 g of butadiene, 2 g of itaconic acid and 0.5 g of carbon tetrachloride was added dropwise at a rate of 40 g per hour at a temperature of 60° C. with stirring. After the lapse of 8 hours, the temperature of the resulting mixture was raised to 70° C. and maintained at said temperature for 30 minutes, and then lowered to room temperature to obtain a polymer emulsion. The polymer emulsion is named "Polymer Emulsion E".

A cement paste was prepared in the same manner as in Example 57, except that Polymer Emulsion E was substituted for the Polymer Emulsion D. This cement paste is named "Sample 39".

EXAMPLE 61

A polymer emulsion was synthesized in the same manner as in the synthesis of a polymer emulsion in Example 60, except that the amount of sodium dodecylbenzenesulfonate was changed to 2 g. A cement paste was prepared in the same manner as in Example 57, except that the thus obtained polymer emulsion was substituted for the Polymer Emulsion D. This cement paste is named "Sample 40".

COMPARATIVE EXAMPLE 13

A polymer emulsion was synthesized in the same manner as in the synthesis of a polymer emulsion in Example 60, except that the amount of sodium dodecylbenzenesulfonate was changed to 3 g. A cement paste for comparison was prepared in the same manner as in Example 57, except that the thus obtained polymer emulsion was substituted for the Polymer Emulsion D. This cement paste is named "Comparative Sample 12".

The flow values of Samples 39 and 40 and Comparative Sample 12 were measured in the same manner as in Table 7. The results obtained were as shown in Table 13.

TABLE 13

| | Amount of surfactant per 100 parts by weight of polymerizable monomer (part by weight) | Stirring time (min) | Flow value (mm) |
|---|---|---|---|
| Sample 39 | 0.5 | 3 | 140 |
| | | 30 | 128 |
| Sample 40 | 1.0 | 3 | 135 |
| | | 30 | 120 |
| Comparative Sample 12 | 1.5 | 3 | 127 |
| | | 30 | 113 |

EXAMPLE 62

A polymer emulsion was synthesized in the same manner as in the synthesis of a polymer emulsion in Example 57, except that polyoxyethylene lauryl ether was substituted for the sodium dodecylbenzenesulfonate and that butyl acrylate was substituted for the ethyl acrylate. A cement paste was prepared in the same manner as in Example 57, except that the thus obtained polymer emulsion was substituted for the Polymer Emulsion D. This cement paste is named "Sample 41".

The flow values of Sample 41 was measured in the same manner as in Table 7 to find that the flow values where the stirring times were 3 minutes, 30 minutes and 60 minutes were 168 mm, 165 mm and 148 mm, respectively.

EXAMPLE 63

A cement paste was prepared in the same manner as in Example 57, except that the Dispersant B was replaced by a commercially available dispersant "Mighty 150" (manufactured by Kao Soap Co., Ltd.) consisting of a high-condensate of sodium napthalenesulfonate. The cement paste is named "Sample 42".

COMPARATIVE EXAMPLE 14

A cement paste for comparison was prepared in the same manner as in Example 63, except that the Polymer Emulsion D was not used. The cement paste is named "Comparative Sample 13".

EXAMPLE 64

A cement paste was prepared in the same manner as in Example 57, except that the Dispersant B was replaced by a commercially available dispersant NP20" (Nisso Master Builders Co., Ltd.) consisting of a condensate of sodium melaminesulfonate. The cement paste is named "Sample 43".

COMPARATIVE EXAMPLE 15

A cement paste for comparison was prepared in the same manner as in Example 63, except that the Polymer Emulsion D was not used. The cement past is named "Comparative Sample 14".

EXAMPLE 65

A cement paste was prepared in the same manner as in Example 57, except that the Dispersant B was replaced by a commercially available dispersant "Plastocrete NC" (manufactured by Nihon Sika Co., Ltd.) consisting of sodium lignin sulfonate. The cement paste is named "Sample 44".

COMPARATIVE EXAMPLE 16

A cement paste for comparison was prepared in the same manner as in Example 65, except that the Polymer Emulsion D was not used. The cement paste is named "Comparative Sample 15".

The flow values of Samples 42 to 44 and Comparative Samples 13 to 15 were measured in the same manner as in Table 7. The results obtained were as shown in Table 14.

TABLE 14

|  | Stirring time (min) | Flow value (mm) |
| --- | --- | --- |
| Sample 42 | 3 | 165 |
|  | 30 | 150 |
|  | 60 | 120 |
| Comparative Sample 13 | 3 | 155 |
|  | 30 | 110 |
| Sample 43 | 3 | 155 |
|  | 30 | 145 |
|  | 60 | 130 |
| Comparative Sample 14 | 3 | 135 |
|  | 30 | 120 |
| Sample 44 | 3 | 115 |
|  | 30 | 103 |
| Comparative Sample 15 | 3 | 100 |
|  | 30 | 87 |

EXAMPLE 66

In a 1-liter autoclave were placed 400 g of water and 1.0 g of potassium persulfate, and polymerization was effected by continuously dropping thereinto a mixed solution of 196 g of ethyl acrylate, 4 g of methacrylic acid and 2 g of dodecylmercaptan at a temperature of 80° C. with stirring over a period of 2 hours, to obtain a polymer emulsion. The polymerization conversion reached 100% in 3 hours after the initiation of the polymerization. The polymer emulsion is named "Polymer Emulsion F".

To 500 g of a normal portland cement (manufactured by chichibu cement Co., Ltd.) were added 3.5 g of Dispersant B and 0.35 g (as solids) of Polymer Emulsion F, and 125 g of water was further added, after which the resulting mixture was stirred at a revolution rate of 120 r.p.m. to prepare a cement paste. This cement paste is named "Sample 45".

EXAMPLE 67

A polymer emulsion was synthesized in the same manner as in the synthesis of a polymer emulsion in Example 66, except that a mixed solution of 194 g of ethyl acrylate, 6 g of acrylic acid and 2 g of dodecylmercaptan was used. A cement paste was prepared in the same manner as in Example 66, except that the thus obtained polymer emulsion was substituted for the Polymer Emulsion F. This cement paste is named "Sample 46".

EXAMPLE 68

A polymer emulsion was synthesized in the same manner as in the synthesis of a polymer emulsion in Example 66, except that a mixed solution of 24 g of ethyl acrylate, 4 g of methacrylic acid, 172 g of styrene and 2 g of dodecylmercaptan was used. A cement paste was prepared in the same manner as in Example 66, except that the thus obtained polymer emulsion was substituted for the Polymer Emulsion F. This cement paste is named "Sample 47".

EXAMPLE 69

A polymer emulsion was synthesized in the same manner as in the synthesis of a polymer emulsion in Example 66, except that a mixed solution of 100 g of ethyl acrylate, 4 g of methacrylic acid, 96 g of styrene and 2 g of dodecylmercaptan was used. A cement paste was prepared in the same manner as in Example 66, except that the thus obtained polymer emulsion was substituted for the Polymer Emulsion F. This cement paste is named "Sample 48".

EXAMPLE 70

A polymer emulsion was synthesized in the same manner as in the synthesis of a polymer emulsion in Example 66, except that a mixed solution of 199 g of ethyl acrylate, 1 g of methacrylic acid and 2 g of dodecylmercaptan was used. A cement paste was prepared in the same manner as in Example 66, except that the thus obtained polymer emulsion was substituted for the Polymer Emulsion F. This cement paste is named "Sample 49".

EXAMPLE 71

A polymer emulsion was synthesized in the same manner as in the synthesis of a polymer emulsion in Example 66, except that a mixed solution of 164 g of butyl acrylate, 36 g of methacrylic acid and 0.4 g of dodecylmercaptan was used. A cement paste was prepared in the same manner as in Example 66, except that the thus obtained polymer emulsion was substituted for the Polymer Emulsion F. This cement paste is named "Sample 50".

EXAMPLE 72

A polymer emulsion was synthesized in the same manner as in the synthesis of a polymer emulsion in Example 66, except that a mixed solution of 196 g of butyl acrylate, 4 g of methacrylic acid and 2 g of dodecylmercaptan was used. A cement paste was prepared in the same manner as in Example 66, except that the thus obtained polymer emulsion was substituted for the Polymer Emulsion F. This cement paste was named "Sample 51".

The flow values of Samples 45 to 51 were measured in the same manner as in Table 7. The results obtained were as shown in Table 15.

TABLE 15

|  | Stirring time (min) | Flow value (mm) |
| --- | --- | --- |
| Sample 45 | 30 | 185 |
|  | 60 | 185 |
|  | 90 | 165 |
| Sample 46 | 30 | 189 |
|  | 60 | 188 |
|  | 90 | 178 |
| Sample 47 | 30 | 150 |
|  | 60 | 138 |
| Sample 48 | 30 | 162 |
|  | 60 | 145 |
| Sample 49 | 30 | 188 |
|  | 60 | 186 |
| Sample 50 | 30 | 176 |
|  | 60 | 176 |
| Sample 51 | 30 | 168 |
|  | 60 | 156 |

EXAMPLE 73

A polymer emulsion was synthesized in the same manner as in the synthesis of a polymer emulsion in Example 66, except that 1 g of sodium benzenesulfonate was added to water. A cement paste was prepared in the same manner as in Example 66, except that the thus obtained polymer emulsion was substituted for the Polymer Emulsion F. This cement paste is named "Sample 52".

EXAMPLE 74

A polymer emulsion was synthesized in the same manner as in the synthesis of a polymer emulsion in Example 66, except that 2 g of sodium dodecylbenzenesulfonate was added to water. A cement paste was prepared in the same manner as in Example 66, except that the thus obtained polymer emulsion was substituted for the Polymer Emulsion F. This cement paste is named "Sample 53".

The flow values of Samples 52 and 53 were measured in the same manner as in Table 7. The results obtained were as shown in Table 16.

TABLE 16

|  | Stirring time (min) | Flow value (mm) |
|---|---|---|
| Sample 52 | 30 | 165 |
|  | 60 | 157 |
| Sample 53 | 30 | 160 |
|  | 60 | 148 |

EXAMPLE 75

A cement paste was prepared in the same manner as in Example 66, except that the Dispersant B was replaced by a commercially available dispersant "Mighty 150" (manufactured by Kao Soap Co., Ltd.) consisting of a high-condensate of sodium napthalenesulfonate. The cement paste is named "Sample 54".

COMPARATIVE EXAMPLE 17

A cement paste for comparison was prepared in the same manner as in Example 75, except that the Polymer Emulsion F was not used. The cement paste is named "Comparative Sample 16".

EXAMPLE 76

A cement paste was prepared in the same manner as in Example 66, except that the Dispersant B was replaced by a commercially available dispersant "NP20" (manufactured by Nisso Master Builders Co., Ltd.) consisting of a condensate of sodium melaminesulfonate. The cement paste is named "Sample 55".

COMPARATIVE EXAMPLE 18

A cement paste for comparison was prepared in the same manner as in Example 76, except that the Polymer Emulsion F was not used. The cement paste is named "Comparative Sample 17".

EXAMPLE 77

A cement paste was prepared in the same manner as in Example 66, except that the Dispersant B was replaced by a commercially available dispersant "Plastocrete NC" (manufactured by Nihon Sika Co., Ltd.) consisting of sodium lignin sulfonate. The cement paste is named "Sample 56".

COMPARATIVE EXAMPLE 19

A cement paste for comparison was prepared in the same manner as in Example 77, except that the Polymer Emulsion F was not used. The cement paste is named "Comparative Sample 18".

The flow values of Samples 54 to 56 and Comparative Samples 16 to 18 were measured in the same manner as in Table 7. The results obtained were as shown in Table 17.

TABLE 17

|  | Stirring time (min) | Flow value (mm) |
|---|---|---|
| Sample 54 | 3 | 175 |
|  | 30 | 160 |
|  | 60 | 130 |
| Comparative Sample 16 | 3 | 155 |
|  | 30 | 110 |
| Sample 55 | 3 | 165 |
|  | 30 | 155 |
|  | 60 | 140 |
| Comparative Sample 17 | 3 | 135 |
|  | 30 | 120 |
| Sample 56 | 3 | 125 |
|  | 30 | 118 |
| Comparative Sample 18 | 3 | 100 |
|  | 30 | 87 |

EXAMPLE 78

To 500 g of a normal portland cement (manufactured by Chichibu Cement Co., Ltd.) were added 3.5 g of the Na salt of a polymer obtained in Example 22 (dispersant) and 0.35 g of Polymer Emulsion C, after which 125 g of water was added to the resulting mixture. The mixture thus obtained was stirred at a revolution rate of 120 r.p.m. to prepare a cement paste. The flow values of the cement paste were measured in the same manner as mentioned above to obtain the results in Table 18.

TABLE 18

| Stirring time (min) | Flow value (mm) |
|---|---|
| 3 | 165 |
| 30 | 160 |
| 60 | 145 |

EXAMPLE 79

To 500 g of a normal portland cement (manufactured by Chichibu Cement Co., Ltd.) were added 3.5 g of Sample 1 (dispersant) and 0.35 g (as solids) of Polymer Emulsion C, after which 125 g of water was added to the resulting mixture. The mixture thus obtained was stirred at a revolution rate of 120 r.p.m. to prepare a cement paste. The flow values of the cement paste were measured in the same manner as mentioned above to obtain the results shown in Table 19.

TABLE 19

| Stirring time (min) | Flow value (mm) |
|---|---|
| 3 | 160 |
| 30 | 156 |
| 60 | 131 |

EXAMPLE 80

To 500 g of a normal portland cement (manufactured by Chichibu Cement Co., Ltd.) were added 3.5 g of the Na salt of the polymer obtained in Example 28 (dispersant) and 0.35 g (as solids) of Polymer Emulsion C, after which 125 g of water was added to the resulting mixture. The mixture thus obtained was stirred at a revolution rate of 120 r.p.m. to prepare a cement paste. The flow values of the cement paste were measured in the same manner as mentioned above to obtain the results shown in Table 20.

TABLE 20

| Stirring time (min) | Flow value (mm) |
| --- | --- |
| 3 | 165 |
| 30 | 160 |
| 60 | 145 |

What is claimed is:

1. A sulfonation product of a polymer of a cyclopentadiene derivative represented by the formula (A) or (B):

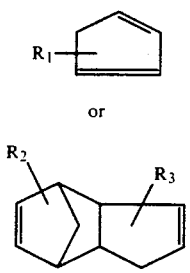

wherein $R_1$ is a hydrogen atom or an alkyl group having 1 to 3 carbon atoms, and $R_2$ and $R_3$, which may be identical or different, are hydrogen atoms or alkyl groups having 1 to 3 carbon atoms.

2. A compound according to claim 1, which is a polymer or copolymer of a sulfonated dicyclopentadiene represented by the formula:

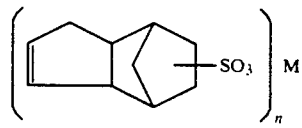

wherein M is hydrogen, an alkali metal, an alkaline earth metal, ammonium or an amine; and n is 1 or 2 and when M is an alkaline earth metal n is 2.

3. A process for producing a polymer or copolymer of a sulfonation product of dicyclopentadiene, which comprises polymerizing a sulfonated dicyclopentadiene represented by the formula:

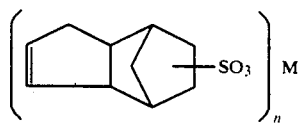

wherein M is hydrogen, an alkali metal, an alkaline earth metal, ammonium or an amine; and n is 1 or 2 and when M is an alkaline earth metal n is 2, or copolymerizing said sulfonated dicyclopentadiene with at least one monomer copolymerizable therewith, in the presence of an acidic compound catalyst.

4. A surfactant for dispersing cement particles in water which comprises a polymer or copolymer of a sulfonated dicyclopentadiene monomer of the formula:

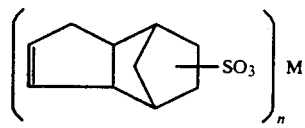

wherein n is 1 or 2 and M is selected from a group consisting of hydrogen, an alkali metal, an alkaline earth metal, ammonia and an amine provided that when M is an alkaline earth metal N is 2.

5. A sulfonation product of a copolymer of a cyclopentadiene derivative represented by the general formula:

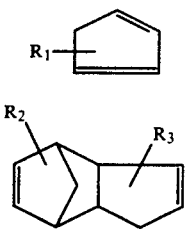

wherein $R_1$ is hydrogen or an alkyl group having 1 to 3 carbon atoms, and $R_2$ and $R_3$ which may be identical or different are hydrogen or alkyl groups having 1 to 3 carbon atoms, with at least one monomer copolymerizable therewith in such a proportion that the weight ratio of the cyclopentadiene derivative to the copolymer is 100/140 or more.

6. A process for producing a sulfonation product of a polymer of a cyclopentadiene derivative, which comprises polymerizing a cyclopentadiene derivative represented by the general formula:

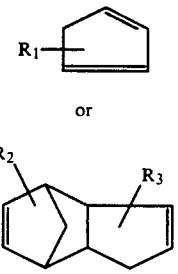

wherein $R_1$ is hydrogen or an alkyl group having 1 to 3 carbon atoms and $R_2$ and $R_3$ which may be the same or different are hydrogen or an alkyl group having 1 to 3 carbon atoms, in the presence of an acidic compound catalyst, and then sulfonating the resulting polymer.

7. A process for producing a sulfonation product of a copolymer of a cyclopentadiene derivative which comprises copolymerizing a cyclopentadiene derivative of the general formula:

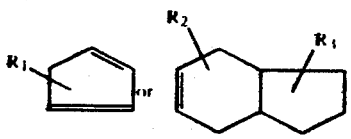

wherein $R_1$ is hydrogen or an alkyl group of 1 to 3 carbon atoms, and $R_2$ and $R_3$ which may be the same or different are hydrogen or an alkyl group of 1–3 carbon atoms with at least one polymerizable monomer in such a proportion that the weight ratio of the cyclopentadiene derivative to the copolymer is 100/140 or more, in the presence of an acidic compound catalyst, and then sulfonating the resulting copolymer.

8. A surfactant for dispersing cement particles in water which comprises a polymer of a sulfonated cyclopentadiene monomer of the formula:

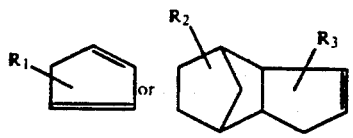

wherein $R_1$ is hydrogen or an alkyl group of 1 to 3 carbon atoms and $R_2$ and $R_3$ which may be the same or different are hydrogen or an alkyl group of 1 to 3 carbon atoms.

9. A surfactant for dispersing cement particles in water which comprises a sulfonated product of a copolymer of a cyclopentadiene monomer of the formula:

or

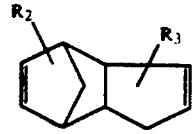

wherein $R_1$ is hydrogen or an alkyl group of 1 to 3 carbon atoms and $R_2$ and $R_3$ which may be the same or different are hydrogen or an alkyl group of 1 to 3 carbon atoms which polymer has a weight ratio of the cyclopentadiene to the copolymer of 100/140.

* * * * *